US012640228B2

(12) United States Patent
Nicoletti et al.

(10) Patent No.: US 12,640,228 B2
(45) Date of Patent: May 26, 2026

(54) POLYMORPHIC MARKERS FOR PHARMACOGENETIC HLA RISK ALLELES

(71) Applicant: Sema4 OpCo, Inc.

(72) Inventors: Paola Nicoletti, Rye, NY (US); Stuart A. Scott, NY, NY (US)

(73) Assignee: Sema4 OpCo, Inc., Stamford, CT (US)

( * ) Notice: Subject to any disclaimer, the term of this patent is extended or adjusted under 35 U.S.C. 154(b) by 1034 days.

(21) Appl. No.: 17/616,615

(22) PCT Filed: Jun. 4, 2020

(86) PCT No.: PCT/US2020/036127
§ 371 (c)(1),
(2) Date: Dec. 3, 2021

(87) PCT Pub. No.: WO2020/247635
PCT Pub. Date: Dec. 10, 2020

(65) Prior Publication Data
US 2022/0228207 A1     Jul. 21, 2022

Related U.S. Application Data

(60) Provisional application No. 62/915,171, filed on Oct. 15, 2019, provisional application No. 62/884,661, filed on Aug. 8, 2019, provisional application No. 62/858,326, filed on Jun. 7, 2019.

(51) Int. Cl.
| | |
|---|---|
| *G16B 20/20* | (2019.01) |
| *C12Q 1/6883* | (2018.01) |
| *G16B 20/40* | (2019.01) |

(52) U.S. Cl.
CPC ........... *G16B 20/20* (2019.02); *C12Q 1/6883* (2013.01); *C12Q 2600/106* (2013.01); *C12Q 2600/156* (2013.01); *C12Q 2600/172* (2013.01); *G16B 20/40* (2019.02)

(58) Field of Classification Search
CPC ............ C12Q 1/6883; C12Q 2600/106; C12Q 2600/156; C12Q 2600/172; C12Q 1/6881; C12Q 1/6858; C12Q 1/6827; G16B 20/20; G16B 20/40; G16B 20/00; G16B 40/20; G16B 40/30; G16H 20/10; G16H 70/40; G16H 10/60; G16H 15/00; G16H 20/70; G16H 50/20; G16H 50/70; A61P 25/18; A61P 25/24
See application file for complete search history.

(56) References Cited

U.S. PATENT DOCUMENTS

2015/0105271 A1*   4/2015  Floratos ............... C12Q 1/6883
                                                                  506/2
2016/0376656 A1*  12/2016  Fang ........................ C12Q 1/68

FOREIGN PATENT DOCUMENTS

| KR | 20190048509 A | 5/2019 |
|---|---|---|
| WO | 2013129542 A1 | 9/2013 |
| WO | WO-2020247635 A1 | 12/2020 |

OTHER PUBLICATIONS

Leckband SG, et al. Clinical Pharmacogenetics Implementation Consortium guidelines for HLA-B genotype and carbamazepine dosing. Clin Pharmacol Ther. Sep. 2013;94(3):324-8. Epub May 21, 2013 (Year: 2013).*

Liu X, et al. Tag SNPs for HLA-B alleles that are associated with drug response and disease risk in the Chinese Han population. Pharmacogenomics J. Oct. 2015;15(5):467-72 (Year: 2015).*

Abi-Rached L, et al. Immune diversity sheds light on missing variation in worldwide genetic diversity panels. PLoS One. Oct. 26, 2018;13(10):e0206512 (Year: 2018).*

Erlichster M, et al. Cross-ethnicity tagging SNPs for HLA alleles associated with adverse drug reaction. Pharmacogenomics J. Jun. 2019;19(3):230-239. Epub. Aug. 10, 2018. [supp.] (Year: 2018).*

Extended European Search Report, EP Patent Application No. 20818019.0, dated Aug. 30, 2023, pp. 1-13.

PCT International Search Report and Written Opinion, International Application No. PCT/US2020/036127, dated Oct. 30, 2020, 17 Pages.

Mushiroda et al. Association of HLA-A*31:01 Screening with the incidence of Carbamazepine-Induced Cutaneous Adverse Reactions in a Japanese Population, JAMA Neurology, Jul. 2018, vol. 75, No. 7, pp. 842-849. Especially p. 843 col. 1 para 2, p. 843 col. 2 para 2, p. 843 col. 2 para 3, p. 845 col. 1 para 1, p. 846 col. 2 para 1, p. 847 col. 1 para 2, Abstract.

Supplementary Partial European Search Report, EP Patent Application No. 20818019.0, pp. 1-16, dated May 26, 2023.

Erlichster Michael et al: "Cross-ethnicity tagging SNPs for HLA alleles associated with adverse drug reaction", The Pharmacogenomics Journal, Nature Publishing Group, GB, vol. 19, No. 3, Aug. 10, 2018 (Aug. 10, 2018), pp. 230-239, XP036847089, ISSN: 1470-269X, DOI: 10.1038/S41397-018-0039-Z.

(Continued)

*Primary Examiner* — Anne M. Gussow
*Assistant Examiner* — Emma R Hoppe
(74) *Attorney, Agent, or Firm* — Wilson Sonsini Goodrich & Rosati

(57) ABSTRACT

We have identified panels of proxy single nucleotide polymorphisms (SNPs) that are highly predictive of particular HLA risk alleles, and concordant across multi-ethnic populations. Accordingly, methods are provided involving clinical DNA testing for HLA panel markers to assess risk for life-threatening adverse drug reactions associated with the human leucocyte antigen (HLA) alleles HLA-B*57:01, HLA-B*15:02, HLA-A*31:01 and HLA-B*58:01. Methods of treating a subject with a drug associated with an adverse drug reaction (ADR) are provided. Based on the assessed risk to a subject for developing an adverse drug reaction in response to a drug, appropriate administrations of the drug can be made. In some embodiments of the method, the drug is administered when there is a low assessed risk of ADR in the subject. Alternatively, when there is a high assessed risk of ADR in the subject, a reduced dosage of the drug, or no drug, can be administered.

8 Claims, 1 Drawing Sheet

(56) References Cited

OTHER PUBLICATIONS

1000 Genomes Project Consortium. A global reference for human genetic variation. Nature 526(7571):68-74 (2015).

Abi-Rached, Laurent et al. Immune diversity sheds light on missing variation in worldwide genetic diversity panels. PloS one 13(10): e0206512, 1-11 (2018).

Bettinotti, Maria P. et al. Characterization of 108 Genomic DNA Reference Materials for 11 Human Leukocyte Antigen Loci: A GeT-RM Collaborative Project. The Journal of molecular diagnostics 20(5):703-715 (2018).

Bykova, Nadia A. et al. In Silico Analysis of the Minor Histocompatibility Antigen Landscape Based on the 1000 Genomes Project. Frontiers in immunology 9:1819, 1-12 (2018).

Gourraud, Pierre-Antoine. et al. HLA diversity in the 1000 genomes dataset. PloS one 9(7): e97282, 1-8 (2014).

PCT/US2020/036127 International Preliminary Report on Patentability dated Dec. 16, 2021.

Whirl-Carrillo, M. et al. Pharmacogenomics knowledge for personalized medicine. Clinical pharmacology and therapeutics 92(4):414-417 (2012).

* cited by examiner

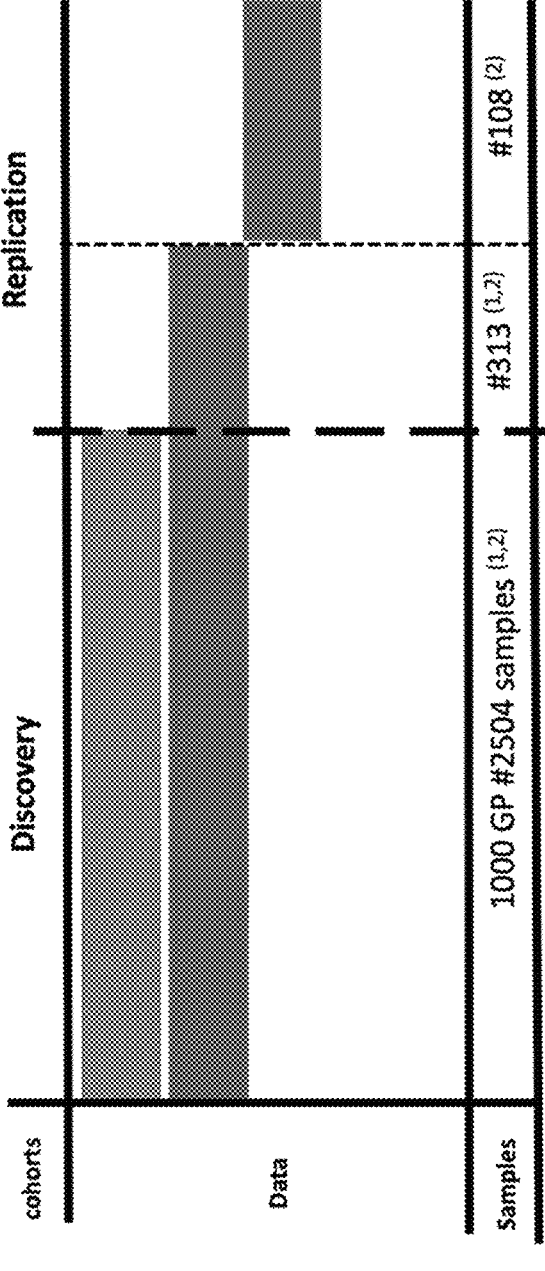

POLYMORPHIC MARKERS FOR PHARMACOGENETIC HLA RISK ALLELES

CROSS REFERENCE TO RELATED APPLICATIONS

This application is a national phase entry of International Application No. PCT/US2020/036127, filed Jun. 4, 2020, which claims the benefit of U.S. Provisional Application No. 62/858,326, filed Jun. 7, 2019; U.S. Provisional Application No. 62/884,661 filed Aug. 8, 2019; and U.S. Provisional Application No. 62/915,171 filed Oct. 15, 2019 which are each incorporated by reference herein in their entireties.

INTRODUCTION

Pharmacogenetics offers the potential to improve health outcomes by identifying individuals who are at greater risk of developing side effects and/or predicting the efficacy of medicines. The growing scientific literature supporting the validity of pharmacogenetics for selected medications has prompted recent clinical practice guidelines for genotype-directed prescribing. In addition, a growing number of approved medications have pharmacogenetic information included on the FDA label. Many of the medications with very high evidence supporting a pharmacogenetic effect are associated with specific HLA risk alleles, which are major risk factors for several life-threatening drug-specific immune-mediated adverse events (e.g., acute hepatitis, hypersensitivity syndrome, Stevens-Johnson syndrome (SJS), and toxic epidermal necrolysis (TEN)).

Clinical guidelines and FDA/EMA testing recommendations are available for several adverse events such as abacavir-induced hypersensitivity syndrome (associated with HLA-B*57:01), carbamazepine or phenytoin induced SJS/TEN (associated with HLA-B*15:02), carbamazepine-induced SJS/TEN (associated with HLA-A*31:01), and allopurinol-induced SJS/TEN (associated with HLA-B*58:01).

Routine HLA typing for pharmacogenomic risk prediction is not cost-effective due to the technical challenges associated with interrogating the polymorphic HLA gene region. The technical challenges are due to the highly polymorphic nature of the HLA gene family region on chromosome 6p. To facilitate pharmacogenomic HLA allele screening, some single nucleotide polymorphisms (SNPs) have been associated with the most relevant HLA risk alleles. However, those proxy-SNPs have inadequate specificity and sensitivity within and across multi-ethnic populations, which has limited their use in clinical practice.

SUMMARY

Drug-induced hypersensitivity reactions can be life-threating adverse events that have been strongly associated with specific human leucocyte antigen (HLA) alleles such as HLA-B*57:01 (abacavir), HLA-B*15:02 (carbamazepine, phenytoin) and HLA-A*31:01 (carbamazepine), and HLA-B*58:01 (allopurinol). We have identified panels of proxy single nucleotide polymorphisms (SNPs) that are highly predictive of particular HLA risk alleles, and concordant across multi-ethnic populations.

Accordingly, the present disclosure describes methods involving clinical DNA testing for the HLA panel markers to assess or predict risk for life-threatening adverse drug reactions associated with the human leucocyte antigen (HLA) alleles HLA-B*57:01, HLA-B*15:02, HLA-A*31:01 and HLA-B*58:01. Methods of treating a subject with a drug associated with an adverse drug reaction (ADR) are provided. Based on the assessed risk to a subject for developing an adverse drug reaction in response to a drug, a suitable dosage regimen for administration of the drug can be selected. In some embodiments of the method, the drug is administered when there is a low assessed risk of ADR in the subject. Alternatively, when there is a high assessed risk of ADR in the subject, a reduced dosage of the drug, or no drug, or an alternative therapy can be administered.

BRIEF DESCRIPTION OF THE DRAWINGS

These and other features, aspects, and advantages of the present disclosure will become better understood with regard to the following description, and accompanying drawings.

FIG. 1 shows a schematic of the datasets utilized in the analysis leading to identification of panels of proxy single nucleotide polymorphisms (SNPs) for HLA risk alleles. (1) Gourraud, et al., 2014, "HLA diversity in the 1000 genomes dataset", PLoS One 9(7): e97282. (2) Abi-Rached, et al., 2018, "Immune diversity sheds light on missing variation in worldwide genetic diversity panels", PLoS One 13(10): e0206512. (3) Bettinotti, et al., 2018, "Characterization of 108 Genomic DNA Reference Materials for 11 Human Leukocyte Antigen Loci: A GeT-RM Collaborative Project", J. Mol. Diagn. 20(5):703-715.

DETAILED DESCRIPTION

Drug-induced hypersensitivity reactions can be life-threating adverse events that have been strongly associated with specific human leucocyte antigen (HLA) alleles such as HLA-B*57:01, HLA-B*15:02 and HLA-A*31:01, and HLA-B*58:01.

We analyzed the 1000 Genome project dataset including samples across super populations with whole genome sequencing and HLA typing data (see e.g., FIG. 1, discovery cohort). The HLA allele tagging performance of each variant within MHC region (n=608,256) was assessed, and their carriage sensitivity and specificity estimated. False positive and false negative samples were typed to confirm the predicted estimations for the best proxy-SNPs. We then genotyped those identified proxy-SNPs on 79 multiethnic samples, 60 of which carry at least one of the four HLA alleles (FIG. 1, replication cohort) to confirm sensibility and sensitivity in an independent cohort.

Based on this analysis, we have identified panels of proxy single nucleotide polymorphisms (SNPs) that are highly predictive of particular HLA risk alleles, and concordant across multi-ethnic populations. As summarized above, this disclosure provides methods that include assessing the subject for pharmacogenetic HLA risk alleles associated with an adverse drug reaction (ADR).

Pharmacogenomic Human Leucocyte Antigen (HLA) Alleles

The HLA system is a gene complex encoding the major histocompatibility complex (MHC) proteins in humans, cell-surface proteins responsible for the regulation of the immune system. The HLA gene complex is located on a 3 Mbp section within chromosome 6p21. HLA genes are highly polymorphic allowing them to fine-tune the adaptive immune system. The HLA-A gene is located on the short arm of chromosome 6 and encodes the larger, α-chain, constituent of HLA-A. Over 2000 variants (alleles) of HLA-A are known, and all alleles receive at least a four-digit classification. More than 1000 alleles of HLA-B gene are known, each of which is given a particular number (such as HLA-B27). Closely related alleles are categorized together; for example, at least 28 very similar alleles are subtypes of HLA-B27. These subtypes are designated as HLA-B*27:01 to HLA-B*27:28.

HLA-A*31:01

The HLA-A*31:01 allele predisposes a subject to multiple phenotypes of carbamazepine hypersensitivity including maculopapular exanthema, hypersensitivity syndrome, and SJS/TEN in a range of populations including Europeans, Japanese, South Koreans and Han Chinese, although the effect size varies between the different phenotypes and populations. The HLA-A*31:01 allele has been shown to be a strong predictor of both mild and severe adverse reactions to carbamazepine, such as the DRESS syndrome form of severe cutaneous reactions. For patients who test positive for HLA-A*31:01, alternative treatments to CBZ are available.

HLA-B*15:02

The presence of HLA-B*15:02 allele is considered a risk factor for development of Stevens-Johnson syndrome/toxic epidermal necrolysis (SJS/TEN) in patients taking aromatic anticonvulsant drugs like carbamazepine and phenytoin.

Carbamazepine (CBZ) is a sodium channel inhibitor, and is an anticonvulsant medication used primarily in the treatment of epilepsy and neuropathic pain. Serious skin reactions such as Stevens-Johnson syndrome (SJS) or toxic epidermal necrolysis (TEN) due to CBZ therapy are more common in people with a particular human leukocyte antigen alleles, such as HLA-B*1502. HLA-B*1502 occurs almost exclusively in people with ancestry across broad areas of Asia, but has a very low or absent frequency in European, Japanese, Korean and African populations. Screening for HLA-B*15:02 is mandated in patients from South East Asia because of a strong association of CBZ hypersensitivity with SJS and TEN.

HLA-B*57:01

The HLA-B*57:01 variant occurs in about 6% of individuals of European or Asian descent.

Abacavir is a nucleoside reverse transcriptase inhibitor (NRTI) that is widely used in combination with other antiretroviral agents to achieve viral suppression and immunologic improvement in HIV therapy. Abacavir has been linked to potentially fatal hypersensitivity reactions (HSR), and is thought to induce HSR by altering self-peptides presented to T-cells, resulting in an immune response. This effect is heightened in patients carrying HLA-B*57:01 due to a direct, metabolism-independent and non-covalent interaction of abacavir with HLA-B*57:01.

HLA-B*58:01

The frequency of the HLA-B*58:01 allele varies between ethnicities. Han Chinese and Thai populations have HLA-B*58:01 allele frequencies of around 8%, as compared to European and Japanese populations, who have allele frequencies of around 1.0% and 0.5%, respectively.

Subjects with one or two copies of the HLA-B*58:01 allele have an increased risk of hypersensitivity reactions, such as Stevens-Johnson Syndrome, toxic epidermal necrolysis or maculopapular eruption, when treated with lamotrigine.

Allopurinol is a purine analog inhibitor of xanthine oxidase that is used to decrease high blood uric acid levels, e.g., in the treatment and/or prevention of gout, specific types of kidney stones, and side effects of chemotherapy.

Allopurinol associated SCAR (severe cutaneous adverse drug reaction) including Stevens-Johnson syndrome (SJS)

and toxic epidermal necrolysis (TEN) has been shown to be associated with the HLA-B*58:01 allele.

Polymorphic Markers for HLA Alleles

Described in the experimental section below are details of the analysis that lead to the identification of polymorphic markers in linkage disequilibrium (LD) with particular pharmacogenomic HLA risk alleles associated with ADRs. Linkage Disequilibrium refers to a non-random association of genetic variations or alleles at different loci in a given population. Such genetic variations and alleles are said to be in linkage disequilibrium when their frequency of association is higher or lower than what would be expected if they were independent and associated randomly.

Table 6 shows specificity and sensitivity for selected proxy-SNPs for HLA-B*57:01, HLA-B*15:02, HLA-A*31:01 and HLA-B*58:01. Table 7 shows sensibility and sensitivity data by ethnicity for the selected proxy-SNPs. In general, the data shows consistency across multi-ethnic populations.

Aspects of this disclosure include assaying for genetic markers in a sample from a subject in order to assess whether the subject has a pharmacogenomic HLA risk allele associated with an ADR.

In some embodiments, the HLA allele is HLA-A*31:01, and the one or more markers in LD are selected from rs114776910_G, rs138415245_G, rs12665140_A, rs147023494_T, rs148590958_C and rs114716190_G. In some embodiments, the one or more markers in LD with HLA-A*31:01 are 2 or more markers, 3 or more markers, 4 or more markers, 5 or more markers, or 6 or more markers.

In some embodiments, the HLA allele is HLA-B*15:02, and the one or more markers in LD are selected from rs144012689_A, rs151107659_A, rs188729361_A and rs181377228_A. In some embodiments, the one or more markers in LD with HLA-B*15:02 are 2 or more markers, 3 or more markers, or 4 or more markers.

In some embodiments, the HLA allele is HLA-B*58:01, and the one or more markers in LD are selected from rs78090769_T, rs79815527_A, rs75412754_C, and rs6936478_A. In some embodiments, the one or more markers in LD with HLA-B*58:01 are 2 or more markers, 3 or more markers, or 4 or more markers.

In some embodiments, the HLA allele is HLA-B*57:01, and the one or more markers in LD are selected from rs115986568_A, rs149663102_T, rs114170382_A, rs114607072_T, rs138099588_G, rs41558312_G, rs58102217_A, and rs41543314_G. In some embodiments, the one or more markers in LD with HLA-B*57:01 are 2 or more markers, 3 or more markers, 4 or more markers, 5 or more markers, 6 or more markers, 7 or more markers, or 8 or more markers.

Tables 1-4 show expanded groups of polymorphic markers that are in linkage disequilibrium (LD) with HLA-A*31:01, HLA-B*15:02, HLA-B*57:01, or HLA-B*58:01, respectively, listed according to the specificity and sensitivity values determined in the analysis.

In some embodiments, the HLA allele is HLA-A*31:01, and the one or more markers in LD are selected from Table 1. In some embodiments, the one or more markers in LD with HLA-A*31:01 are selected from markers numbered 1 to 100 of Table 1, such as markers numbered 1 to 50, 1 to 40, 1 to 30, 1 to 20, 1 to 15, 1 to 10, 1 to 8, or 1 to 6 of Table 1. In some embodiments, the one or more markers of Table 1 in LD with HLA-A*31:01 are 2 or more markers, such as 3 or more, 4 or more, 5 or more, 6 or more, 7 or more, 8 or more, 10 or more, 12 or more, 15 or more, 20 or more, 30 or more, 40 or more, 50 or more, 100 or more markers.

In some embodiments, the HLA allele is HLA-B*15:02, and the one or more markers in LD are selected from Table 2. In some embodiments, the one or more markers in LD with HLA-B*15:02 are selected from markers numbered 1 to 100 of Table 2, such as markers numbered 1 to 50, 1 to 40, 1 to 30, 1 to 20, 1 to 15, 1 to 10, 1 to 8, 1 to 6, or 1 to 4 of Table 2. In some embodiments, the one or more markers of Table 2 in LD with HLA-B*15:02 are 2 or more markers, such as 3 or more, 4 or more, 5 or more, 6 or more, 7 or more, 8 or more, 10 or more, 12 or more, 15 or more, 20 or more, 30 or more, 40 or more, 50 or more, 100 or more, 150 or more, or 200 or more markers.

In some embodiments, the HLA allele is HLA-B*57:01, and the one or more markers in LD are selected from Table 3. In some embodiments, the one or more markers in LD with HLA-B*57:01 are selected from markers numbered 1 to 100 of Table 3, such as markers numbered 1 to 50, 1 to 40, 1 to 30, 1 to 20, 1 to 15, 1 to 10, or 1 to 8 of Table 3. In some embodiments, the one or more markers of Table 3 in LD with HLA-B*57:01 are 2 or more markers, such as 3 or more, 4 or more, 5 or more, 6 or more, 7 or more, 8 or more, 10 or more, 12 or more, 15 or more, 20 or more, 30 or more, 40 or more, 50 or more, 100 or more, 150 or more, or 200 or more markers.

In some embodiments, the HLA allele is HLA-B*58:01, and the one or more markers in LD are selected from Table 4. In some embodiments, the one or more markers in LD with HLA-B*58:01 are selected from markers numbered 1 to 15 of Table 4, such as markers numbered 1 to 12, 1 to 10, 1 to 8, 1 to 6, or 1 to 4 of Table 4. In some embodiments, the one or more markers of Table 4 in LD with HLA-B*58:01 are 2 or more markers, such as 3 or more, 4 or more, 5 or more, 6 or more, 7 or more, 8 or more, 10 or more, or 12 or more markers.

Table 5 shows a group of polymorphic markers that are in linkage disequilibrium (LD) with HLA-A*58:02, listed according to the specificity and sensitivity values determined in the analysis. In some embodiments, the polymorphic markers of Table 5 can be utilized to distinguish a subject predicted to carry a different allele, e.g., HLA-A*58:01. In some embodiments, the method includes assessing whether one or more markers in LD with HLA-B*58:02 and selected from Table 4 are absent. In some embodiments, an assessment of the presence or absence of one or more markers in LD with HLA-B*58:02 provides an indication of whether or not the subject carries the allele HLA-B*58:01 that is associated with an ADR.

When assessing a subject for the presence of absence of a particular HLA allele, the number and selection of markers that can be utilized as proxy for that HLA allele can depend in part on the specificity and/or sensitivity values of the markers. In some embodiments, markers having specificity and/or sensitivity values of 95% or more, such as 96% or more, 97% or more, 98% or more, 98.5% or more, 99% or more, or 99.5% or more, are assessed and provide a high probability of the presence of the HLA allele with which the markers are in LD. In some embodiments, markers having PPV and/or NPV values of 95% or more, such as 96% or more, 97% or more, 98% or more, 98.5% or more, 99% or more, or 99.5% or more, are assessed and provide a high probability of the presence or absence of the HLA allele with which the markers are in LD.

Aspects of this disclosure include panels of genetic markers that are capable of providing cost effective and rapid genotype-based screening for multiple pharmacogenomic HLA risk alleles associated with ADRs.

In some embodiments, the HLA allele status of the subject for two or more of the HLA risk alleles HLA-A*31:01, HLA-B*15:02, HLA-B*57:01, and HLA-B*58:01 is identified using the methods and panels of this disclosure, such as 2, 3 or all of the HLA risk alleles HLA-A*31:01, HLA-B*15:02, HLA-B*57:01, and HLA-B*58:01. In some embodiments, the panel includes one or more genetic markers of two of Tables 1-4. In some embodiments, the panel includes one or more genetic markers of three of Tables 1-4. In some embodiments, the panel includes one or more genetic markers of each of Tables 1-4.

In some embodiments, the panel includes 4 or more genetic markers of Table 6, such as 5 or more, 10 or more, or 15 or more. In some embodiments, the panel of Table 6 includes at least one genetic marker for each of the HLA risk alleles HLA-A*31:01, HLA-B*15:02, HLA-B*57:01, and HLA-B*58:01. In some embodiments, the panel of Table 6 includes two or more genetic markers for each of the HLA risk alleles HLA-A*31:01, HLA-B*15:02, HLA-B*57:01, and HLA-B*58:01, such as 3 or more, or 4 or more genetic markers for each of the HLA risk alleles.

Aspects of the disclosure include panels of oligonucleotide probes that are complementary to the panels of genetic markers of Table 6 (e.g., described herein).

Risk Assessment

Aspects of this disclosure include assaying for the presence or absence of particular genetic markers in a subject, and thus predicting or assessing the presence or absence of pharmacogenomic HLA risk alleles in the subject. A high probability of the presence of a pharmacogenomic HLA risk allele in the subject can indicate a high risk of ADR associated with allele. A low risk of ADR for the subject can be assessed when the subject lacks a panel of genetic markers in LD with the pharmacogenomic HLA risk allele.

Tables 1-7 provide lists of genetic markers of interest in LD with the pharmacogenomic HLA risk alleles and ranked according to specificity, sensitivity, PPV and NPV scores, as shown. A positive predictive value (PPV) is the probability that a subject with a positive screening test for the genetic marker truly have the pharmacogenomic HLA risk allele. A negative predictive value (NPV) is the probability that a subject with a negative screening test for the genetic marker truly have the pharmacogenomic HLA risk allele.

The level of risk of the ADR in a subject can be assessed qualitatively or quantitively based on the results of assaying for the genetic markers described herein. In some embodiments, one or more of the genetic markers of Tables 1-7 in LD with a particular HLA risk allele are assayed, and a high risk of the ADR is assessed when all of the genetic markers that are assayed are determined to be present. In some embodiments, one or more of the genetic markers of Table 6 in LD with a particular HLA risk allele are assayed, and a low risk of the ADR is assessed when all of the genetic markers that are assayed are determined to be absent. In some embodiments, the one or more genetic markers are 2 or more, such as 3, 4, 5, 6, 7, 8, 9, 10 or more markers.

In some embodiments, the HLA allele is HLA-A*31:01, and the one or more markers in LD that are assayed and determined to be present (or absent) are selected from rs114776910_G, rs138415245_G, rs12665140_A, rs147023494_T, rs148590958_C and rs114716190_G. In some embodiments, the one or more markers in LD with HLA-A*31:01 that are assayed and determined to be present (or absent) are 2 or more markers, such as 3, 4, 5, or 6 markers.

In some embodiments, the HLA allele is HLA-B*15:02, and the one or more markers in LD that are assayed and determined to be present (or absent) are selected from rs144012689_A, rs151107659_A, rs188729361_A and rs181377228_A. In some embodiments, the one or more markers in LD with HLA-B*15:02 that are assayed and determined to be present (or absent) are 2 or more markers, such as 3, or 4 markers.

In some embodiments, the HLA allele is HLA-B*58:01, and the one or more markers in LD that are assayed and determined to be present (or absent) are selected from rs78090769_T, rs79815527_A, rs75412754_C, and rs6936478_A. In some embodiments, the one or more markers in LD with HLA-B*58:01 that are assayed and determined to be present (or absent) are 2 or more markers, such as 3, or 4 markers.

In some embodiments, the HLA allele is HLA-B*57:01, and the one or more markers in LD that are assayed and determined to be present (or absent) are selected from rs115986568_A, rs149663102_T, rs114170382_A, rs114607072_T, rs138099588_G, rs41558312_G, rs58102217_A, and rs41543314_G. In some embodiments, the one or more markers in LD with HLA-B*57:01 that are assayed and determined to be present (or absent) are 2 or more markers, such as 3, 4, 5, 6, 7, or 8 markers.

It is understood that a HLA risk score for a subject can be assessed or calculated, based at least in part on the number of individual markers or SNPs (e.g., as described herein) that are assessed, weighted according to the relative predictive strengths of the markers or SNPs (e.g., their PPV and NPV values). The risk score can represent a probability that a particular HLA risk allele is present or absent in the subject. A variety of methods for calculating such risk scores are available to the skilled artisan. In some embodiments, the risk is assessed across a multi-ethnic population. In some embodiments, the risk is assessed across a particular ethnicity. The genetic markers described herein can be highly predictive of particular HLA risk alleles, and concordant across multi-ethnic populations, avoiding the possibility of false positive or negative results within ethnicities that are not concordant.

In some embodiments, the subject has a low risk of an ADR when the risk that the associated HLA allele is absent is assessed with a risk score probability of 0.5 or more, such as 0.6 or more, 0.7 or more, 0.8 or more, 0.9 or more, 0.95 or more, 0.96 or more, 0.98 or more, 0.99 or more, or 1.0.

In some embodiments, the subject has a high risk of an ADR when the risk that the associated HLA allele is present is assessed with a risk score probability of 0.5 or more, such as 0.6 or more, 0.7 or more, 0.8 or more, 0.9 or more, 0.95 or more, 0.96 or more, 0.98 or more, 0.99 or more, or 1.0.

In some embodiments, all of the genetic markers of Table 6 in LD with HLA-A*31:01 are assayed, and a high risk of the ADR is assessed when all of the genetic markers are determined to be present. In some embodiments, all of the genetic markers of Table 6 in LD with HLA-A*31:01 are assayed, and a low risk of the ADR is assessed when none of the genetic markers are determined to be present.

In some embodiments, all of the genetic markers of Table 6 in LD with HLA-B*15:02 are assayed, and a high risk of the ADR is assessed when all of the genetic markers are determined to be present. In some embodiments, all of the genetic markers of Table 6 in LD with HLA-B*15:02 are assayed, and a low risk of the ADR is assessed when none of the genetic markers are determined to be present.

In some embodiments, all of the genetic markers of Table 6 in LD with HLA-B*57:01 are assayed, and a high risk of the ADR is assessed when all of the genetic markers are determined to be present. In some embodiments, all of the genetic markers of Table 6 in LD with HLA-B*57:01 are assayed, and a low risk of the ADR is assessed when none of the genetic markers are determined to be present.

In some embodiments, all of the genetic markers of Table 6 in LD with HLA-B*58:01 are assayed, and a high risk of the ADR is assessed when all of the genetic markers are determined to be present. In some embodiments, all of the genetic markers of Table 6 in LD with HLA-B*58:01 are assayed, and a low risk of the ADR is assessed when none of the genetic markers are determined to be present.

SNP Assays

Polymorphic sites (PS) and SNPs described herein can be identified according to the SNP NCBI database. As recognized by the skilled artisan, nucleic acid samples containing a particular PS may be complementary double stranded molecules and thus reference to a particular site on the sense strand refers as well to the corresponding site on the complementary antisense strand. Similarly, reference to a particular genotype obtained for a PS on both copies of one strand of a chromosome is equivalent to the complementary genotype obtained for the same PS on both copies of the other strand.

The sequences of the genetic markers (e.g., SNPs) recited herein, as well as their complementary sequence, may be used to design probes and primers for genotyping the markers in a nucleic acid sample obtained from a human subject of interest using any of a variety of methods well known in the art that permits the determination of whether the individual has at least one copy of the genetic marker. Nucleic acid molecules utilized in such methods generally include RNA, genomic DNA, or cDNA derived from RNA.

Typically, genotyping methods involve assaying a nucleic acid sample prepared from a biological sample obtained from the individual to determine the identity of a nucleotide or nucleotide pair present at one or more polymorphic sites of interest. Nucleic acid samples may be prepared from virtually any biological sample. The genetic sample can be obtained from a biological sample selected from blood, hair, skin, saliva, semen, urine, fecal material, sweat, and buccal sample. In some embodiments, the sample is an oral tissue sample, scraping, or wash or a biological fluid sample, preferably saliva, urine or blood.

Nucleic acid samples may be prepared for analysis using any technique known to those skilled in the art. Preferably, such techniques result in the isolation of genomic DNA sufficiently pure for determining the genotype for the desired polymorphic site(s) in the nucleic acid molecule. To enhance the sensitivity and specificity of that determination, it is frequently desirable to amplify from the nucleic acid sample a target region containing the PS to be genotyped.

Any amplification technique known to those of skill in the art may be used in practicing the present invention including, but not limited to, polymerase chain reaction (PCR) techniques. Other suitable amplification methods include the ligase chain reaction (LCR), transcription amplification, self-sustained sequence replication, isothermal methods, and nucleic acid-based sequence amplification (NASBA).

In some embodiments, the presence or absence of a polynucleotide is identified by amplifying or failing to amplify an amplification product from the sample, where the amplification product is preferably digested with a restriction enzyme before analysis and/or where the SNP is identified by hybridizing the nucleic acid sample with a primer label which is a detectable moiety. In some embodiments, the presence or absence of the polynucleotide is identified by hybridization to specific Hairloop™ probes spotted on a microarray, by allele-specific PCR, by KASP genotyping chemistry or TaqMan Assays.

9

Administration Methods

This disclosure provides methods including administration of a drug associated with an ADR (e.g., as described herein) to a subject, e.g., to treat the subject for a disease or condition without significant adverse side effects. Drugs that may be administered to the subject according to the methods of this disclosure include, but are not limited to, aromatic anticonvulsant drugs such as carbamazepine and phenytoin, allopurinol, abacavir, and pharmaceutically acceptable salts thereof.

In some embodiments, the drug is an aromatic anticonvulsant drug. In some embodiments, the drug is carbamazepine. Carbamazepine can be used to treat subjects for epilepsy, bipolar disorder, or conditions associated with nerve pain such as trigeminal neuralgia.

In some embodiments, the drug is phenytoin. Phenytoin can be used to treat subjects for epilepsy, or conditions associated with anxiety control and mood stabilization.

In some embodiments, the drug is a nucleoside reverse transcriptase inhibitor (NRTI). In some embodiments, the drug is abacavir. Abacavir can be used to treat subjects for HIV and AIDS.

In some embodiments, the drug is an inhibitor of xanthine oxidase. In some embodiments, the drug is allopurinol. Allopurinol can be used to treat subjects for primary or secondary gout (acute attacks, tophi, joint destruction, uric acid lithiasis, and/or nephropathy).

Based on the assessed risk to a subject for developing an adverse drug reaction in response to a drug, a suitable dosage regimen for administration of the drug can be selected. In some embodiments of the method, the drug is administered with a normal dosage when there is a low assessed risk of ADR in the subject. By normal dosage is meant a dosage of a particular drug that is medically appropriate to administer to a subject having an average level of risk for ADR as compared to a reference population, e.g., without regard to an elevated level of risk of ADR as described herein.

In some embodiments of the method, when there is a high assessed risk of ADR in the subject, a reduced dosage of the drug. In some embodiments of the method, when there is a high assessed risk of ADR in the subject, the drug associated with the ADR is not administered to the subject. In some embodiments of the method, when there is a high assessed risk of ADR in the subject, an alternative therapy or drug can be administered.

Definitions

Hypersensitivity is an extreme form of adaptive immune response occurring when the immune system reacts inappropriately to certain antigens, and may lead to inflammatory reactions and tissue damage.

The term "biological sample" refers to any biological sample that can be isolated from an individual, including samples from which genetic material may be isolated. A "genetic sample" refers to DNA and/or RNA obtained or derived from an individual.

The terms "treat" and "treating" mean to administer a therapeutic agent, such as a drug described herein, internally or externally to an individual in need of the therapeutic agent. Typically, the therapeutic agent is administered in a therapeutically effective amount, which means an amount effective to produce one or more beneficial results. The therapeutically effective amount of a particular agent may vary according to factors such as the disease state, age, and weight of the patient being treated, and the sensitivity of the patient, e.g., ability to respond, to the therapeutic agent. Whether a beneficial or clinical result has been achieved can be assessed by any clinical measurement typically used by physicians, physician's assistants or other skilled healthcare providers to assess the presence, severity or progression status of the targeted disease, symptom or adverse effect. Typically, a therapeutically effective amount of an agent will result in an improvement in the relevant clinical measurement(s) over the baseline status, or over the expected status if not treated, of at least 5%, usually by at least 10%, more usually at least 20%, most usually at least 30%, preferably at least 40%), more preferably at least 50%, most preferably at least 60%, ideally at least 70%, more ideally at least 80%, and most ideally at least 90%. While an embodiment of the present disclosure (e.g., a treatment method or article of manufacture) may not achieve the desired clinical benefit or result in every patient, it should do so in a statistically significant number of patients as determined by any statistical test known in the art such as the likelihood ratio test based logistic regression with 2 degree freedom, etc.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It must be noted that, as used in the specification and the appended claims, the singular forms "a," "an" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1: Multi-Ethnic Single Nucleotide Polymorphism (SNP)-Based Screening of Pharmacogenomic HLA Alleles Implicated in Drug-Induced Hypersensitivity Reactions Abstract:

Drug-induced hypersensitivity reactions are life-threating adverse events that have been strongly associated with specific human leucocyte antigen (HLA) alleles. Among the reported pharmacogenomic HLA risk alleles, clinical practice guidelines and/or FDA/EMA testing recommendations are currently available for HLA-B*57:01 (abacavir), HLA-B*15:02 (carbamazepine, phenytoin) and HLA-A*31:01 (carbamazepine), and HLA-B*58:01 (allopurinol). However, routine HLA typing for pharmacogenomic risk prediction is not cost-effective due to the technical challenges with interrogating the polymorphic HLA gene region. To facilitate pharmacogenomic HLA allele screening, previous studies identified single nucleotide polymorphisms (SNPs) in linkage disequilibrium with the most relevant HLA risk alleles; however, these proxy-SNPs have inadequate sensitivity across multi-ethnic populations and poor specificity, which has limited their use in clinical practice. To identify a multi-ethnic panel of proxy-SNPs for HLA-B*57:01, HLA-B*15:02, HLA-A*31:01 and HLA-B*58:01, publicly available whole genome sequencing and HLA typing data from the 1000 Genomes (1KG) Project were interrogated (Abi-Rached et al., 2018, "Immune diversity sheds light on missing variation in worldwide genetic diversity panels", PLoS One 13(10):e0206512; Bettinotti et al., 2018, "Characterization of 108 Genomic DNA Reference Materials for 11 Human Leukocyte Antigen Loci: A GeT-RM Collaborative Project", J. Mol. Diagn. 20(5):703-715; Bykova et al., 2018, "In Silico Analysis of the Minor Histocompatibility Antigen Landscape Based on the 1000 Genomes Project", Front Immunol. 9:1819; Genomes Project et al., 2015, "A global reference for human genetic variation", Nature 526 (7571):68-74; Gourraud et al., 2014, "HLA diversity in the 1000 genomes dataset", PLoS One 9(7):e97282).

The sensitivity and specificity of all SNPs in the MHC region (n=608,256) were initially assessed across a multi-ethnic subset of 1KG subjects (n=1079), which identified a panel of 18 proxy-SNPs that detected the four pharmacogenomic HLA risk alleles with a mean sensitivity and specificity of 99%.

Selected false positive and negative 1KG samples were clarified by confirmatory genotyping (Agena Bioscience), which resulted in the proxy-SNP panel having sensitivity and specificity >99% for HLA-B*57:01 ($N_{carriers}$=69; $N_{SNPs}$=8), HLA-B*15:02 ($N_{carriers}$=65; $N_{SNPs}$=3) and HLA-A*31:01 ($N_{carriers}$=88; $N_{SNPs}$=4); and >95% for HLA-B*58:01 ($N_{carriers}$=77; $N_{SNPs}$=3). The validity of the proxy-SNP panel was confirmed in an independent 1KG subset (n=1425), and in the combined cohort (n=2504) the majority of proxy-SNPs had 100% sensitivity and 99% specificity for the four pharmacogenomic HLA alleles in the Asian, European and Hispanic populations. Importantly, the panel also included proxy-SNPs with 98% sensitivity and specificity for HLA-A*31:01 and HLA-B*58:01 in the African population. Taken together, these data indicate that the identified novel proxy-SNP panel could provide cost-effective and rapid genotype-based screening to predict pharmacogenomic HLA allele risk in diverse patient populations.

Summary: The Sema4 pharmacogenetic HLA panel described herein predicts specific HLA alleles by a haplotype of markers, which improves the positive and negative predictive values. The Sema4 pharmacogenetic HLA panel markers are very concordant across multi-ethnic populations. A series of polymorphic markers were identified in LD with four pharmacogenetic HLA alleles (see e.g., Tables 1-4) implicated in life-threatening adverse drug reactions. Sensitive and specific haplotype analysis using this novel pharmacogenetic HLA panel could be a cost-effective and rapid genotype-based screening test to predict pharmacogenetic HLA allele carrier status across multi-ethnic populations. The pharmacogenetic HLA panel could also be extended to other indications (as appropriate), as these HLA risk alleles are involved in additional severe adverse drug reactions as well as susceptibility/prognosis for some complex diseases.

TABLE 1

Polymorphic markers in LD with HLA-A*31:01. PPV and NPV refer to positive and negative predictive values, respectively. Markers 1-6 of table 1 provide a panel of preferred markers for HLA-A*31:01.

| Marker | SNP | specificity | sensitivity | ppv | npv |
|---|---|---|---|---|---|
| 1 | rs114776910_G | 0.998 | 0.968 | 0.968 | 0.998 |
| 2 | rs138415245_G | 0.998 | 0.960 | 0.968 | 0.997 |
| 3 | rs148590958_C | 0.998 | 0.952 | 0.967 | 0.997 |
| 4 | rs114716190_G | 0.998 | 0.952 | 0.967 | 0.997 |
| 5 | rs12665140_A | 0.997 | 0.960 | 0.960 | 0.997 |
| 6 | rs147023494_T | 0.996 | 0.992 | 0.939 | 0.999 |
| 7 | rs117117960_A | 0.998 | 0.912 | 0.974 | 0.995 |
| 8 | rs185367427_C | 0.985 | 0.992 | 0.781 | 0.999 |
| 9 | rs17179220_A | 0.980 | 0.968 | 0.726 | 0.998 |
| 10 | rs74345156_G | 0.907 | 1 | 0.365 | 1 |
| 11 | rs28733991_A | 0.906 | 1 | 0.362 | 1 |
| 12 | rs72495971_G | 0.905 | 1 | 0.36 | 1 |
| 13 | rs140821968_T | 0.905 | 1 | 0.358 | 1 |
| 14 | rs144608908_CATGT | 0.904 | 1 | 0.357 | 1 |
| 15 | rs17179816_T | 0.893 | 0.984 | 0.328 | 0.999 |

TABLE 1-continued

Polymorphic markers in LD with HLA-A*31:01. PPV and
NPV refer to positive and negative predictive values,
respectively. Markers 1-6 of table 1 provide a panel
of preferred markers for HLA-A*31:01.

| Marker | SNP | specificity | sensitivity | ppv | npv |
|---|---|---|---|---|---|
| 16 | rs12665039__C | 0.890 | 0.984 | 0.322 | 0.999 |
| 17 | rs6916499__C | 0.869 | 0.983 | 0.316 | 0.998 |
| 18 | rs1059449__A | 0.889 | 1 | 0.323 | 1 |
| 19 | rs41541222__T | 0.889 | 1 | 0.323 | 1 |
| 20 | rs7760172__C | 0.887 | 1 | 0.320 | 1 |
| 21 | rs142270424__A | 0.887 | 1 | 0.320 | 1 |
| 22 | rs116432652__T | 0.887 | 0.992 | 0.318 | 0.999 |
| 23 | rs77899164__C | 0.887 | 1 | 0.319 | 1 |
| 24 | rs10677323__CAG | 0.887 | 1 | 0.319 | 1 |
| 25 | rs17185784__G | 0.887 | 1 | 0.319 | 1 |
| 26 | rs28544296__C | 0.887 | 1 | 0.319 | 1 |
| 27 | rs72492287__A | 0.887 | 1 | 0.319 | 1 |
| 28 | rs115691105__T | 0.887 | 1 | 0.319 | 1 |
| 29 | rs28555376__C | 0.887 | 1 | 0.319 | 1 |
| 30 | rs2571375__G | 0.886 | 0.873 | 0.290 | 0.992 |
| 31 | rs72495912__A | 0.886 | 1 | 0.318 | 1 |
| 32 | rs75134279__C | 0.886 | 1 | 0.317 | 1 |
| 33 | rs72492295__T | 0.886 | 1 | 0.317 | 1 |
| 34 | rs151233761__C | 0.886 | 1 | 0.317 | 1 |
| 35 | rs74185225__C | 0.886 | 1 | 0.317 | 1 |
| 36 | rs72492302__C | 0.886 | 1 | 0.317 | 1 |
| 37 | rs72495906__G | 0.886 | 0.992 | 0.315 | 0.999 |
| 38 | rs147862323__C | 0.885 | 1 | 0.316 | 1 |
| 39 | rs115980375__C | 0.885 | 1 | 0.316 | 1 |
| 40 | rs116363141__A | 0.885 | 1 | 0.316 | 1 |
| 41 | rs72495910__C | 0.885 | 1 | 0.316 | 1 |
| 42 | rs76665055__T | 0.885 | 1 | 0.315 | 1 |
| 43 | rs11758504__T | 0.885 | 1 | 0.315 | 1 |
| 44 | rs138348864__A | 0.885 | 1 | 0.315 | 1 |
| 45 | rs192326368__T | 0.884 | 1 | 0.315 | 1 |
| 46 | rs72495975__T | 0.884 | 1 | 0.315 | 1 |
| 47 | rs184553151__T | 0.884 | 1 | 0.314 | 1 |
| 48 | rs11759097__A | 0.884 | 1 | 0.314 | 1 |
| 49 | rs115456943__A | 0.884 | 1 | 0.314 | 1 |
| 50 | rs75298535__C | 0.884 | 1 | 0.314 | 1 |
| 51 | rs551457015__G | 0.884 | 0.992 | 0.312 | 0.999 |
| 52 | rs28896571__T | 0.883 | 1 | 0.313 | 1 |
| 53 | rs28533954__A | 0.883 | 1 | 0.313 | 1 |
| 54 | rs11760172__T | 0.883 | 1 | 0.313 | 1 |
| 55 | rs28688639__G | 0.883 | 1 | 0.313 | 1 |
| 56 | rs11752319__A | 0.883 | 1 | 0.313 | 1 |
| 57 | rs72495983__A | 0.883 | 1 | 0.313 | 1 |
| 58 | rs13194536__T | 0.883 | 1 | 0.312 | 1 |
| 59 | rs74196807__G | 0.883 | 0.992 | 0.310 | 0.999 |
| 60 | rs143182422__T | 0.882 | 1 | 0.311 | 1 |
| 61 | rs77997154__T | 0.875 | 0.992 | 0.301 | 0.999 |
| 62 | rs114839838__A | 0.877 | 0.984 | 0.298 | 0.999 |
| 63 | rs116001094__C | 0.877 | 0.984 | 0.298 | 0.999 |
| 64 | rs9259811. rs141296323__A | 0.870 | 1 | 0.295 | 1 |
| 65 | rs12663276__G | 0.875 | 1 | 0.299 | 1 |
| 66 | rs74211750__G | 0.875 | 1 | 0.299 | 1 |
| 67 | rs201477120__G | 0.875 | 1 | 0.299 | 1 |
| 68 | rs427995__C | 0.868 | 1 | 0.290 | 1 |
| 69 | rs79437615__G | 0.875 | 1 | 0.298 | 1 |
| 70 | rs74218766__T | 0.875 | 1 | 0.298 | 1 |
| 71 | rs79231337__C | 0.875 | 1 | 0.298 | 1 |
| 72 | rs41272547__A | 0.875 | 1 | 0.298 | 1 |
| 73 | rs41562315__A | 0.875 | 1 | 0.298 | 1 |
| 74 | rs41543916__A | 0.875 | 1 | 0.298 | 1 |
| 75 | rs41543412__G | 0.875 | 1 | 0.298 | 1 |
| 76 | rs1061235__T | 0.875 | 1 | 0.298 | 1 |
| 77 | rs77309262__T | 0.875 | 1 | 0.298 | 1 |
| 78 | rs10947038__A | 0.875 | 0.984 | 0.295 | 0.999 |
| 79 | rs11757135__T | 0.875 | 0.984 | 0.295 | 0.999 |
| 80 | rs17179957__A | 0.875 | 0.984 | 0.295 | 0.999 |
| 81 | rs189990623__T | 0.875 | 1 | 0.297 | 1 |
| 82 | rs114058671__A | 0.875 | 1 | 0.297 | 1 |
| 83 | rs79857957__T | 0.875 | 1 | 0.297 | 1 |
| 84 | rs78993465__A | 0.875 | 1 | 0.297 | 1 |
| 85 | rs115694430__G | 0.875 | 1 | 0.297 | 1 |
| 86 | rs72500497__T | 0.875 | 0.984 | 0.294 | 0.999 |
| 87 | rs199947646__T | 0.875 | 0.984 | 0.294 | 0.999 |
| 88 | rs183401702__A | 0.875 | 0.984 | 0.294 | 0.999 |
| 89 | rs11756376__G | 0.875 | 0.984 | 0.294 | 0.999 |
| 90 | rs116451203__C | 0.875 | 0.984 | 0.294 | 0.999 |
| 91 | rs143328784__T | 0.875 | 0.984 | 0.294 | 0.999 |
| 92 | rs149964608__A | 0.875 | 0.984 | 0.294 | 0.999 |
| 93 | rs200286021__G | 0.874 | 1 | 0.297 | 1 |
| 94 | rs72498354__T | 0.874 | 1 | 0.297 | 1 |
| 95 | rs149645832__T | 0.874 | 1 | 0.297 | 1 |
| 96 | rs74295242__A | 0.874 | 1 | 0.297 | 1 |
| 97 | rs115334476__C | 0.874 | 1 | 0.297 | 1 |
| 98 | rs145720557__A | 0.874 | 1 | 0.297 | 1 |
| 99 | rs76895251__C | 0.874 | 1 | 0.297 | 1 |
| 100 | rs72498357__G | 0.874 | 1 | 0.297 | 1 |
| 101 | rs114766850__A | 0.874 | 1 | 0.297 | 1 |
| 102 | rs75367802__A | 0.874 | 0.984 | 0.293 | 0.999 |
| 103 | rs11754264__C | 0.874 | 0.984 | 0.293 | 0.999 |
| 104 | rs72498353__T | 0.874 | 1 | 0.296 | 1 |
| 105 | rs150671547__A | 0.873 | 1 | 0.295 | 1 |
| 106 | rs538730912__A | 0.873 | 0.992 | 0.294 | 0.999 |
| 107 | rs7772638__G | 0.873 | 1 | 0.295 | 1 |
| 108 | rs35114469__T | 0.872 | 1 | 0.293 | 1 |
| 109 | rs140923546__A | 0.872 | 1 | 0.293 | 1 |
| 110 | rs114304833__C | 0.872 | 1 | 0.293 | 1 |
| 111 | rs115106715__T | 0.872 | 1 | 0.293 | 1 |
| 112 | rs115521177__A | 0.872 | 1 | 0.293 | 1 |
| 113 | rs34354617__C | 0.871 | 1 | 0.292 | 1 |
| 114 | rs35575266__C | 0.871 | 1 | 0.292 | 1 |
| 115 | rs114777139__A | 0.871 | 1 | 0.292 | 1 |
| 116 | rs72498352__C | 0.871 | 1 | 0.292 | 1 |
| 117 | rs12665310__C | 0.871 | 1 | 0.292 | 1 |
| 118 | rs376173738__GAT | 0.871 | 0.992 | 0.290 | 0.999 |
| 119 | rs12664958__C | 0.871 | 1 | 0.291 | 1 |
| 120 | rs74202021__A | 0.871 | 1 | 0.291 | 1 |
| 121 | rs11754005__T | 0.870 | 1 | 0.290 | 1 |
| 122 | rs17185650__A | 0.870 | 1 | 0.289 | 1 |
| 123 | rs17179270__G | 0.870 | 1 | 0.289 | 1 |
| 124 | rs12528253__A | 0.870 | 0.984 | 0.286 | 0.999 |
| 125 | rs78455625__A | 0.869 | 1 | 0.288 | 1 |
| 126 | rs78380318__A | 0.868 | 1 | 0.287 | 1 |
| 127 | rs114157794__G | 0.868 | 1 | 0.287 | 1 |
| 128 | rs116252145__C | 0.865 | 0.984 | 0.279 | 0.999 |
| 129 | rs78810446__G | 0.865 | 0.952 | 0.272 | 0.997 |
| 130 | rs12660668__G | 0.864 | 1 | 0.281 | 1 |
| 131 | rs116031481__C | 0.864 | 1 | 0.280 | 1 |
| 132 | rs116076476__A | 0.863 | 0.992 | 0.277 | 0.999 |
| 133 | rs74184772__G | 0.863 | 0.976 | 0.274 | 0.998 |
| 134 | rs115760798__T | 0.862 | 1 | 0.278 | 1 |
| 135 | rs199710390__C | 0.862 | 0.976 | 0.273 | 0.998 |
| 136 | rs72495985__G | 0.862 | 1 | 0.278 | 1 |
| 137 | rs74223603__T | 0.862 | 1 | 0.278 | 1 |
| 138 | rs12662520__T | 0.862 | 1 | 0.278 | 1 |
| 139 | rs72495986__T | 0.862 | 1 | 0.278 | 1 |
| 140 | rs147496146__T | 0.862 | 1 | 0.278 | 1 |
| 141 | rs139102237__T | 0.862 | 1 | 0.278 | 1 |
| 142 | rs6921957__C | 0.862 | 1 | 0.278 | 1 |
| 143 | rs6927115__C | 0.862 | 1 | 0.278 | 1 |
| 144 | rs117143236__C | 0.862 | 1 | 0.278 | 1 |
| 145 | rs115731392__A | 0.862 | 1 | 0.278 | 1 |
| 146 | rs77849405__A | 0.862 | 1 | 0.278 | 1 |
| 147 | rs150655579__A | 0.862 | 1 | 0.278 | 1 |
| 148 | rs151034657__G | 0.862 | 1 | 0.278 | 1 |
| 149 | rs72498350__C | 0.862 | 0.992 | 0.276 | 0.999 |
| 150 | rs3901687__T | 0.862 | 1 | 0.277 | 1 |
| 151 | rs1962778__T | 0.862 | 1 | 0.277 | 1 |
| 152 | rs11758670__C | 0.862 | 1 | 0.277 | 1 |
| 153 | rs35541854__T | 0.862 | 1 | 0.277 | 1 |
| 154 | rs74187129__G | 0.862 | 1 | 0.277 | 1 |
| 155 | rs75525135__G | 0.862 | 1 | 0.277 | 1 |
| 156 | rs74590183__G | 0.862 | 1 | 0.277 | 1 |
| 157 | rs546947741__C | 0.862 | 1 | 0.277 | 1 |
| 158 | rs34146016__C | 0.862 | 1 | 0.277 | 1 |
| 159 | rs6922132__C | 0.861 | 1 | 0.276 | 1 |
| 160 | rs72498347__T | 0.861 | 1 | 0.276 | 1 |

TABLE 1-continued

Polymorphic markers in LD with HLA-A*31:01. PPV and
NPV refer to positive and negative predictive values,
respectively. Markers 1-6 of table 1 provide a panel
of preferred markers for HLA-A*31:01.

| Marker | SNP | specificity | sensitivity | ppv | npv |
|---|---|---|---|---|---|
| 161 | rs147394713_A | 0.858 | 1 | 0.272 | 1 |
| 162 | rs28397212_A | 0.857 | 1 | 0.271 | 1 |
| 163 | rs1611593_A | 0.851 | 1 | 0.268 | 1 |
| 164 | rs115367733_T | 0.857 | 1 | 0.270 | 1 |
| 165 | rs72492286_A | 0.856 | 1 | 0.269 | 1 |
| 166 | rs74206461_T | 0.856 | 1 | 0.269 | 1 |
| 167 | rs17185791_C | 0.855 | 1 | 0.268 | 1 |
| 168 | rs72492285_T | 0.855 | 1 | 0.268 | 1 |
| 169 | rs28678129_A | 0.855 | 1 | 0.268 | 1 |
| 170 | rs72492288_C | 0.855 | 1 | 0.268 | 1 |
| 171 | rs149028986_G | 0.855 | 1 | 0.268 | 1 |
| 172 | rs139978410_T | 0.855 | 1 | 0.268 | 1 |
| 173 | rs28533123_G | 0.854 | 1 | 0.267 | 1 |
| 174 | rs116123788_C | 0.854 | 1 | 0.266 | 1 |
| 175 | rs150513929_C | 0.853 | 1 | 0.265 | 1 |

TABLE 2

Polymorphic markers in LD with HLA-B*15:02. PPV and
NPV refer to positive and negative predictive values,
respectively. In some cases, markers 1-6 of table
2 provide a panel of markers for HLA-B*15:02.

| Marker | SNP | spec | sens | ppv | npv |
|---|---|---|---|---|---|
| 1 | rs144012689_A | 0.999 | 1 | 0.977 | 1 |
| 2 | rs151107659_A | 0.999 | 1 | 0.977 | 1 |
| 3 | rs188729361_A | 0.999 | 0.988 | 0.977 | 0.999 |
| 4 | rs181377228_A | 0.999 | 0.988 | 0.977 | 0.999 |
| 5 | rs190938408_C | 0.994 | 1 | 0.862 | 1 |
| 6 | rs138238859_C | 0.993 | 0.988 | 0.852 | 0.999 |
| 7 | rs371096447_C | 0.998 | 0.943 | 0.965 | 0.997 |
| 8 | rs140855588_G | 0.998 | 0.954 | 0.965 | 0.998 |
| 9 | rs185615899_G | 0.998 | 0.954 | 0.965 | 0.998 |
| 10 | rs186302377_A | 0.998 | 0.954 | 0.965 | 0.998 |
| 11 | rs190335533_A | 0.998 | 0.909 | 0.952 | 0.996 |
| 12 | rs149481627_A | 0.998 | 0.909 | 0.952 | 0.996 |
| 13 | rs191392216_G | 0.998 | 0.943 | 0.954 | 0.997 |
| 14 | rs183151869_G | 0.997 | 0.954 | 0.943 | 0.998 |
| 15 | rs112214065_A | 0.997 | 0.954 | 0.943 | 0.998 |
| 16 | rs185092079_T | 0.997 | 0.943 | 0.932 | 0.997 |
| 17 | rs572250590_TA | 0.997 | 0.943 | 0.922 | 0.997 |
| 18 | rs149203328_T | 0.996 | 0.954 | 0.903 | 0.998 |
| 19 | rs143114181_G | 0.996 | 0.943 | 0.902 | 0.997 |
| 20 | rs191184615_C | 0.996 | 0.886 | 0.896 | 0.995 |
| 21 | rs191579971_G | 0.996 | 0.886 | 0.896 | 0.995 |
| 22 | rs148931659_G | 0.996 | 0.886 | 0.896 | 0.995 |
| 23 | rs189418663_T | 0.995 | 0.897 | 0.868 | 0.996 |
| 24 | rs146122378_A | 0.995 | 0.897 | 0.868 | 0.996 |
| 25 | rs140202631_A | 0.995 | 0.897 | 0.868 | 0.996 |
| 26 | rs192693532_A | 0.995 | 0.897 | 0.868 | 0.996 |
| 27 | rs193043557_C | 0.995 | 0.897 | 0.868 | 0.996 |
| 28 | rs185642961_T | 0.993 | 0.909 | 0.842 | 0.996 |
| 29 | rs150361898_T | 0.993 | 0.988 | 0.844 | 0.999 |
| 30 | rs184043553_C | 0.990 | 0.954 | 0.785 | 0.998 |
| 31 | rs189011516_C | 0.990 | 0.954 | 0.785 | 0.998 |
| 32 | rs149084446_A | 0.990 | 0.954 | 0.785 | 0.998 |
| 33 | rs143205755_G | 0.990 | 0.954 | 0.785 | 0.998 |
| 34 | rs186137290_A | 0.990 | 0.954 | 0.785 | 0.998 |
| 35 | rs144528645_A | 0.990 | 0.954 | 0.785 | 0.998 |
| 36 | rs149186815_A | 0.990 | 0.943 | 0.783 | 0.997 |
| 37 | rs377473202_A | 0.990 | 0.954 | 0.785 | 0.998 |
| 38 | rs185803278_T | 0.990 | 0.954 | 0.785 | 0.998 |
| 39 | rs188083561_C | 0.990 | 0.943 | 0.783 | 0.997 |
| 40 | rs563052401_T | 0.990 | 0.931 | 0.780 | 0.997 |
| 41 | rs183111482_A | 0.990 | 0.954 | 0.777 | 0.998 |
| 42 | rs146215260_G | 0.990 | 0.954 | 0.777 | 0.998 |
| 43 | rs181964803_G | 0.990 | 0.954 | 0.777 | 0.998 |
| 44 | rs373371958_T | 0.990 | 0.977 | 0.781 | 0.999 |
| 45 | rs139479797_A | 0.989 | 1 | 0.771 | 1 |

TABLE 2-continued

Polymorphic markers in LD with HLA-B*15:02. PPV and
NPV refer to positive and negative predictive values,
respectively. In some cases, markers 1-6 of table
2 provide a panel of markers for HLA-B*15:02.

| Marker | SNP | spec | sens | ppv | npv |
|---|---|---|---|---|---|
| 46 | rs148144626_G | 0.987 | 1 | 0.739 | 1 |
| 47 | rs183454889_A | 0.987 | 1 | 0.739 | 1 |
| 48 | rs117246140_A | 0.986 | 1 | 0.727 | 1 |
| 49 | rs139655885_A | 0.985 | 0.988 | 0.719 | 0.999 |
| 50 | rs574446645_T | 0.985 | 0.965 | 0.708 | 0.998 |
| 51 | rs188898809_A | 0.985 | 0.988 | 0.713 | 0.999 |
| 52 | rs146671208_C | 0.985 | 0.977 | 0.710 | 0.999 |
| 53 | rs147099772_A | 0.982 | 0.988 | 0.674 | 0.999 |
| 54 | rs141102944_C | 0.982 | 0.988 | 0.674 | 0.999 |
| 55 | rs535710313_C | 0.982 | 0.977 | 0.671 | 0.999 |
| 56 | rs368752130_T | 0.981 | 0.954 | 0.656 | 0.998 |
| 57 | rs141884536_A | 0.980 | 1 | 0.656 | 1 |
| 58 | rs150140732_C | 0.980 | 0.977 | 0.641 | 0.999 |
| 59 | rs183506958_A | 0.980 | 0.977 | 0.641 | 0.999 |
| 60 | rs188043002_C | 0.980 | 0.977 | 0.641 | 0.999 |
| 61 | rs138563211_T | 0.979 | 0.988 | 0.639 | 0.999 |
| 62 | rs142858529_G | 0.975 | 0.897 | 0.576 | 0.996 |
| 63 | rs117406933_A | 0.970 | 0.920 | 0.529 | 0.997 |
| 64 | rs200098765_CT | 0.970 | 0.954 | 0.538 | 0.998 |
| 65 | rs111959410_A | 0.970 | 0.954 | 0.538 | 0.998 |
| 66 | rs117941869_A | 0.969 | 0.920 | 0.525 | 0.997 |
| 67 | rs146482738_C | 0.969 | 0.920 | 0.525 | 0.997 |
| 68 | rs117321340_C | 0.969 | 0.920 | 0.525 | 0.997 |
| 69 | rs117322540_A | 0.969 | 0.920 | 0.525 | 0.997 |
| 70 | rs117618911_G | 0.969 | 0.920 | 0.525 | 0.997 |
| 71 | rs185998437_T | 0.969 | 0.920 | 0.525 | 0.997 |
| 72 | rs182965382_T | 0.969 | 0.920 | 0.525 | 0.997 |
| 73 | rs73396821_T | 0.969 | 0.954 | 0.535 | 0.998 |
| 74 | rs10484555_C | 0.969 | 0.954 | 0.535 | 0.998 |
| 75 | rs112489947_A | 0.969 | 0.954 | 0.535 | 0.998 |
| 76 | rs113085541_G | 0.969 | 0.954 | 0.535 | 0.998 |
| 77 | rs112351161_C | 0.969 | 0.954 | 0.535 | 0.998 |
| 78 | rs111300804_C | 0.969 | 0.954 | 0.535 | 0.998 |
| 79 | rs113856689_G | 0.969 | 0.954 | 0.535 | 0.998 |
| 80 | rs111990896_C | 0.969 | 0.954 | 0.535 | 0.998 |
| 81 | rs113036952_A | 0.969 | 0.943 | 0.532 | 0.997 |
| 82 | rs73400622_T | 0.969 | 0.943 | 0.532 | 0.997 |
| 83 | rs112254995_G | 0.969 | 0.954 | 0.535 | 0.998 |
| 84 | rs117733669_A | 0.969 | 0.954 | 0.535 | 0.998 |
| 85 | rs142470226_C | 0.969 | 0.909 | 0.519 | 0.996 |
| 86 | rs139287227_C | 0.969 | 0.954 | 0.531 | 0.998 |
| 87 | rs530539237_A | 0.969 | 0.954 | 0.531 | 0.998 |
| 88 | rs142340836_C | 0.968 | 0.909 | 0.516 | 0.996 |
| 89 | rs145372685_T | 0.968 | 0.909 | 0.516 | 0.996 |
| 90 | rs3893132_A | 0.968 | 0.943 | 0.525 | 0.997 |
| 91 | rs185207145_T | 0.968 | 0.931 | 0.522 | 0.997 |
| 92 | rs139021429_C | 0.968 | 0.943 | 0.525 | 0.997 |
| 93 | rs41552817_T | 0.968 | 0.943 | 0.525 | 0.997 |
| 94 | rs11547346_G | 0.968 | 0.943 | 0.525 | 0.997 |
| 95 | rs111715297_C | 0.968 | 0.954 | 0.528 | 0.998 |
| 96 | rs116646009_A | 0.968 | 0.954 | 0.528 | 0.998 |
| 97 | rs113424831_A | 0.968 | 0.954 | 0.525 | 0.998 |
| 98 | rs182442744_T | 0.966 | 0.931 | 0.506 | 0.997 |
| 99 | rs147853218_A | 0.966 | 0.954 | 0.512 | 0.998 |
| 100 | rs112392510_T | 0.966 | 0.954 | 0.512 | 0.998 |
| 101 | rs138594816_A | 0.966 | 0.943 | 0.506 | 0.997 |
| 102 | rs118067913_A | 0.966 | 0.943 | 0.503 | 0.997 |
| 103 | rs117345749_G | 0.966 | 0.931 | 0.5 | 0.997 |
| 104 | rs190925576_A | 0.966 | 0.943 | 0.503 | 0.997 |
| 105 | rs150400725_T | 0.966 | 0.943 | 0.503 | 0.997 |
| 106 | rs138932482_T | 0.966 | 0.943 | 0.503 | 0.997 |
| 107 | rs117573397_A | 0.966 | 0.943 | 0.503 | 0.997 |
| 108 | rs182159831_T | 0.965 | 0.943 | 0.5 | 0.997 |
| 109 | rs180756175_C | 0.965 | 0.943 | 0.5 | 0.997 |
| 110 | rs143350908_T | 0.965 | 0.943 | 0.5 | 0.997 |
| 111 | rs117761656_T | 0.965 | 0.954 | 0.5 | 0.998 |
| 112 | rs117508387_G | 0.965 | 0.954 | 0.5 | 0.998 |
| 113 | rs117514434_C | 0.965 | 0.954 | 0.5 | 0.998 |
| 114 | rs116931476_A | 0.964 | 0.931 | 0.491 | 0.997 |
| 115 | rs117927250_T | 0.964 | 0.931 | 0.491 | 0.997 |
| 116 | rs146502008_A | 0.964 | 0.931 | 0.491 | 0.997 |
| 117 | rs138351562_A | 0.964 | 0.931 | 0.491 | 0.997 |
| 118 | rs117277006_G | 0.964 | 0.931 | 0.491 | 0.997 |

TABLE 2-continued

Polymorphic markers in LD with HLA-B*15:02. PPV and
NPV refer to positive and negative predictive values,
respectively. In some cases, markers 1-6 of table
2 provide a panel of markers for HLA-B*15:02.

| Marker | SNP | spec | sens | ppv | npv |
|---|---|---|---|---|---|
| 119 | rs118004259_A | 0.964 | 0.931 | 0.491 | 0.997 |
| 120 | rs149945194_A | 0.964 | 0.931 | 0.491 | 0.997 |
| 121 | rs117104932_T | 0.964 | 0.931 | 0.491 | 0.997 |
| 122 | rs117952735_T | 0.964 | 0.931 | 0.491 | 0.997 |
| 123 | rs146651644_A | 0.964 | 0.931 | 0.491 | 0.997 |
| 124 | rs137976064_A | 0.964 | 0.931 | 0.491 | 0.997 |
| 125 | rs147827468_G | 0.964 | 0.943 | 0.494 | 0.997 |
| 126 | rs117105459_G | 0.964 | 0.943 | 0.494 | 0.997 |
| 127 | rs141225527_A | 0.964 | 0.943 | 0.494 | 0.997 |
| 128 | rs117304527_T | 0.964 | 0.943 | 0.494 | 0.997 |
| 129 | rs117138694_C | 0.964 | 0.943 | 0.494 | 0.997 |
| 130 | rs116967475_C | 0.964 | 0.943 | 0.494 | 0.997 |
| 131 | rs117876434_T | 0.964 | 0.943 | 0.494 | 0.997 |
| 132 | rs116849356_C | 0.964 | 0.943 | 0.494 | 0.997 |
| 133 | rs188050700_G | 0.964 | 0.943 | 0.494 | 0.997 |
| 134 | rs117311356_A | 0.964 | 0.943 | 0.494 | 0.997 |
| 135 | rs117646937_G | 0.964 | 0.943 | 0.494 | 0.997 |
| 136 | rs116977957_C | 0.964 | 0.943 | 0.494 | 0.997 |
| 137 | rs117062631_T | 0.964 | 0.943 | 0.494 | 0.997 |
| 138 | rs118182436_G | 0.964 | 0.943 | 0.494 | 0.997 |
| 139 | rs116974494_C | 0.964 | 0.943 | 0.494 | 0.997 |
| 140 | rs117131177_C | 0.964 | 0.943 | 0.494 | 0.997 |
| 141 | rs376322896_CT | 0.964 | 0.931 | 0.488 | 0.997 |
| 142 | rs117563601_T | 0.964 | 0.931 | 0.488 | 0.997 |
| 143 | rs117943000_G | 0.964 | 0.943 | 0.491 | 0.997 |
| 144 | rs17192218_T | 0.964 | 0.943 | 0.503 | 0.997 |
| 145 | rs117308456_A | 0.963 | 0.943 | 0.488 | 0.997 |
| 146 | rs73394901_A | 0.961 | 0.954 | 0.474 | 0.998 |
| 147 | rs116969494_A | 0.961 | 0.909 | 0.459 | 0.996 |
| 148 | rs117552809_T | 0.961 | 0.909 | 0.459 | 0.996 |
| 149 | rs3757349_G | 0.961 | 0.909 | 0.459 | 0.996 |
| 150 | rs117585298_T | 0.961 | 0.909 | 0.459 | 0.996 |
| 151 | rs117932423_C | 0.960 | 0.909 | 0.457 | 0.996 |
| 152 | rs73396806_C | 0.959 | 0.954 | 0.464 | 0.998 |
| 153 | rs144724632_G | 0.959 | 0.954 | 0.461 | 0.998 |
| 154 | rs16899202_C | 0.959 | 0.954 | 0.459 | 0.998 |
| 155 | rs75881311_A | 0.955 | 0.909 | 0.430 | 0.996 |
| 156 | rs111343098_G | 0.948 | 0.954 | 0.403 | 0.998 |
| 157 | rs112587708_T | 0.948 | 0.954 | 0.401 | 0.998 |
| 158 | rs111892155_T | 0.948 | 0.954 | 0.401 | 0.998 |
| 159 | rs113727715_T | 0.948 | 0.954 | 0.401 | 0.998 |
| 160 | rs112999185_A | 0.948 | 0.954 | 0.401 | 0.998 |
| 161 | rs113679636_A | 0.948 | 0.954 | 0.401 | 0.998 |
| 162 | rs111603143_A | 0.948 | 0.954 | 0.401 | 0.998 |
| 163 | rs113109076_T | 0.948 | 0.954 | 0.401 | 0.998 |
| 164 | rs111789237_A | 0.948 | 0.954 | 0.401 | 0.998 |
| 165 | rs112491786_G | 0.948 | 0.954 | 0.401 | 0.998 |
| 166 | rs114516477_G | 0.947 | 0.954 | 0.4 | 0.998 |
| 167 | rs112906071_G | 0.947 | 0.954 | 0.4 | 0.998 |
| 168 | rs114617616_G | 0.947 | 0.954 | 0.4 | 0.998 |
| 169 | rs80209589_A | 0.947 | 0.954 | 0.4 | 0.998 |
| 170 | rs58432298_C | 0.947 | 0.954 | 0.4 | 0.998 |
| 171 | rs59994501_G | 0.947 | 0.954 | 0.4 | 0.998 |
| 172 | rs116541664_T | 0.947 | 0.954 | 0.4 | 0.998 |
| 173 | rs59636752_A | 0.947 | 0.954 | 0.4 | 0.998 |
| 174 | rs112544348_G | 0.947 | 0.954 | 0.4 | 0.998 |
| 175 | rs112401274_A | 0.947 | 0.954 | 0.4 | 0.998 |
| 176 | rs113021938_G | 0.947 | 0.954 | 0.4 | 0.998 |
| 177 | rs191524270_C | 0.947 | 0.954 | 0.4 | 0.998 |
| 178 | rs181158919_G | 0.947 | 0.954 | 0.4 | 0.998 |
| 179 | rs143579819_T | 0.947 | 0.954 | 0.4 | 0.998 |
| 180 | rs113370283_A | 0.947 | 0.954 | 0.4 | 0.998 |
| 181 | rs113367014_A | 0.947 | 0.954 | 0.4 | 0.998 |
| 182 | rs527948201_T | 0.947 | 0.954 | 0.4 | 0.998 |
| 183 | rs114199487_A | 0.947 | 0.954 | 0.4 | 0.998 |
| 184 | rs115607159_G | 0.947 | 0.954 | 0.398 | 0.998 |
| 185 | rs112560101_T | 0.947 | 0.954 | 0.398 | 0.998 |
| 186 | rs58792975_A | 0.947 | 0.954 | 0.398 | 0.998 |
| 187 | rs2854021_A | 0.947 | 0.954 | 0.396 | 0.998 |
| 188 | rs60004964_C | 0.942 | 0.909 | 0.366 | 0.996 |
| 189 | rs73397100_A | 0.942 | 0.909 | 0.365 | 0.996 |
| 190 | rs112971796_C | 0.942 | 0.909 | 0.365 | 0.996 |
| 191 | rs57243444_T | 0.942 | 0.909 | 0.365 | 0.996 |

TABLE 2-continued

Polymorphic markers in LD with HLA-B*15:02. PPV and
NPV refer to positive and negative predictive values,
respectively. In some cases, markers 1-6 of table
2 provide a panel of markers for HLA-B*15:02.

| Marker | SNP | spec | sens | ppv | npv |
|---|---|---|---|---|---|
| 192 | rs17200670_T | 0.940 | 0.909 | 0.358 | 0.996 |
| 193 | rs151064822_T | 0.940 | 0.909 | 0.357 | 0.996 |
| 194 | rs149637252_A | 0.923 | 0.909 | 0.301 | 0.996 |
| 195 | rs17198238_G | 0.917 | 0.931 | 0.290 | 0.997 |
| 196 | rs28507710_C | 0.916 | 0.931 | 0.289 | 0.997 |
| 197 | rs60056504_C | 0.915 | 0.988 | 0.297 | 0.999 |
| 198 | rs377634126_G | 0.911 | 0.977 | 0.286 | 0.999 |
| 199 | rs74290509_A | 0.911 | 0.977 | 0.286 | 0.999 |
| 200 | rs146848089_G | 0.911 | 0.977 | 0.285 | 0.999 |
| 201 | rs79022003_C | 0.909 | 0.977 | 0.282 | 0.999 |
| 202 | rs569068189_A | 0.908 | 0.965 | 0.278 | 0.998 |
| 203 | rs371740078_CA | 0.907 | 0.943 | 0.270 | 0.997 |
| 204 | rs183893204_A | 0.898 | 0.863 | 0.236 | 0.994 |
| 205 | rs200226984_C | 0.898 | 0.863 | 0.236 | 0.994 |
| 206 | rs140835803_C | 0.892 | 0.943 | 0.242 | 0.997 |
| 207 | rs28380929_T | 0.872 | 0.943 | 0.212 | 0.997 |
| 208 | rs141986043_GAAA | 0.869 | 0.938 | 0.212 | 0.997 |
| 209 | rs140558131_T | 0.867 | 0.965 | 0.209 | 0.998 |
| 210 | rs184149624_G | 0.866 | 0.965 | 0.208 | 0.998 |
| 211 | rs541741946_T | 0.865 | 0.954 | 0.205 | 0.998 |
| 212 | rs568023593_G | 0.865 | 0.954 | 0.205 | 0.998 |
| 213 | rs3130691_T | 0.865 | 0.954 | 0.205 | 0.998 |
| 214 | rs3130690_T | 0.865 | 0.954 | 0.205 | 0.998 |
| 215 | rs9265141_C | 0.865 | 0.954 | 0.205 | 0.998 |
| 216 | rs545227273_TTG | 0.865 | 0.954 | 0.205 | 0.998 |
| 217 | rs9265147_A | 0.865 | 0.954 | 0.205 | 0.998 |
| 218 | rs2844591_C | 0.865 | 0.954 | 0.205 | 0.998 |
| 219 | rs3998364_T | 0.865 | 0.954 | 0.205 | 0.998 |
| 220 | rs9265190_T | 0.865 | 0.954 | 0.205 | 0.998 |
| 221 | rs9265257_C | 0.865 | 0.954 | 0.205 | 0.998 |
| 222 | rs3094683_G | 0.865 | 0.954 | 0.205 | 0.998 |
| 223 | rs3130704_A | 0.865 | 0.954 | 0.205 | 0.998 |
| 224 | rs9265515_C | 0.865 | 0.954 | 0.205 | 0.998 |
| 225 | rs9265584_C | 0.865 | 0.954 | 0.205 | 0.998 |
| 226 | rs2079174_G | 0.865 | 0.954 | 0.205 | 0.998 |
| 227 | rs2079173_C | 0.865 | 0.954 | 0.205 | 0.998 |
| 228 | rs9265144_C | 0.865 | 0.954 | 0.205 | 0.998 |
| 229 | rs9265348_A | 0.865 | 0.954 | 0.205 | 0.998 |
| 230 | rs9265416_C | 0.865 | 0.954 | 0.205 | 0.998 |
| 231 | rs561443073_T | 0.865 | 0.954 | 0.205 | 0.998 |
| 232 | rs532088383_G | 0.865 | 0.954 | 0.205 | 0.998 |
| 233 | rs9265589_A | 0.864 | 0.954 | 0.204 | 0.998 |
| 234 | rs72847209_C | 0.864 | 0.897 | 0.194 | 0.995 |
| 235 | rs77192564_T | 0.864 | 0.897 | 0.194 | 0.995 |
| 236 | rs9264793_A | 0.860 | 0.897 | 0.189 | 0.995 |
| 237 | rs9264792_A | 0.858 | 0.897 | 0.188 | 0.995 |
| 238 | rs9264871_A | 0.856 | 0.920 | 0.189 | 0.996 |
| 239 | rs9264872_T | 0.856 | 0.920 | 0.189 | 0.996 |
| 240 | rs548484308_T | 0.856 | 0.920 | 0.189 | 0.996 |
| 241 | rs551344396_GAA | 0.856 | 0.943 | 0.193 | 0.997 |
| 242 | rs2524050_C | 0.855 | 0.954 | 0.193 | 0.998 |
| 243 | rs2524043_G | 0.855 | 0.954 | 0.193 | 0.998 |
| 244 | rs1049853_A | 0.855 | 0.943 | 0.191 | 0.997 |
| 245 | rs9264621_C | 0.855 | 0.943 | 0.191 | 0.997 |
| 246 | rs9264639_T | 0.855 | 0.943 | 0.191 | 0.997 |
| 247 | rs1050428_T | 0.855 | 0.943 | 0.191 | 0.997 |
| 248 | rs2253842_A | 0.855 | 0.954 | 0.193 | 0.998 |
| 249 | rs2844602_T | 0.855 | 0.954 | 0.193 | 0.998 |
| 250 | rs2524056_C | 0.855 | 0.954 | 0.193 | 0.998 |
| 251 | rs2524055_C | 0.855 | 0.954 | 0.193 | 0.998 |
| 252 | rs534659501_C | 0.855 | 0.954 | 0.193 | 0.998 |
| 253 | rs2844600_T | 0.855 | 0.954 | 0.193 | 0.998 |
| 254 | rs2853934_T | 0.855 | 0.954 | 0.193 | 0.998 |
| 255 | rs2853932_A | 0.855 | 0.954 | 0.193 | 0.998 |
| 256 | rs146805812_C | 0.855 | 0.954 | 0.193 | 0.998 |
| 257 | rs2844599_C | 0.855 | 0.954 | 0.193 | 0.998 |
| 258 | rs2524048_C | 0.855 | 0.954 | 0.193 | 0.998 |
| 259 | rs2524047_G | 0.855 | 0.954 | 0.193 | 0.998 |
| 260 | rs2844597_T | 0.855 | 0.954 | 0.193 | 0.998 |
| 261 | rs2844596_A | 0.855 | 0.954 | 0.193 | 0.998 |
| 262 | rs2853927_T | 0.855 | 0.954 | 0.193 | 0.998 |
| 263 | rs137962016_C | 0.855 | 0.954 | 0.193 | 0.998 |
| 264 | rs369795453_CT | 0.855 | 0.954 | 0.193 | 0.998 |

TABLE 2-continued

Polymorphic markers in LD with HLA-B*15:02. PPV and
NPV refer to positive and negative predictive values,
respectively. In some cases, markers 1-6 of table
2 provide a panel of markers for HLA-B*15:02.

| Marker | SNP | spec | sens | ppv | npv |
|---|---|---|---|---|---|
| 265 | rs1819788_C | 0.855 | 0.954 | 0.193 | 0.998 |
| 266 | rs2524164_A | 0.855 | 0.954 | 0.193 | 0.998 |
| 267 | rs2524160_A | 0.855 | 0.954 | 0.193 | 0.998 |
| 268 | rs2524155_G | 0.855 | 0.954 | 0.193 | 0.998 |
| 269 | rs2524154_T | 0.855 | 0.954 | 0.193 | 0.998 |
| 270 | rs2524151_A | 0.855 | 0.954 | 0.193 | 0.998 |
| 271 | rs2524148_G | 0.855 | 0.954 | 0.193 | 0.998 |
| 272 | rs9264672_T | 0.854 | 0.943 | 0.191 | 0.997 |
| 273 | rs2853937_C | 0.854 | 0.954 | 0.193 | 0.998 |
| 274 | rs2853930_C | 0.854 | 0.954 | 0.193 | 0.998 |
| 275 | rs2853929_T | 0.854 | 0.954 | 0.193 | 0.998 |
| 276 | rs2524051_G | 0.854 | 0.954 | 0.193 | 0.998 |
| 277 | rs537625500_A | 0.854 | 0.954 | 0.193 | 0.998 |
| 278 | rs140598632_A | 0.854 | 0.954 | 0.192 | 0.998 |
| 279 | rs9264875_C | 0.853 | 0.931 | 0.188 | 0.997 |
| 280 | rs9264876_C | 0.853 | 0.931 | 0.188 | 0.997 |
| 281 | rs9264767_A | 0.852 | 0.954 | 0.190 | 0.998 |
| 282 | rs9264878_T | 0.852 | 0.931 | 0.186 | 0.997 |
| 283 | rs28361006_C | 0.851 | 0.931 | 0.186 | 0.997 |
| 284 | rs28361007_G | 0.851 | 0.931 | 0.186 | 0.997 |
| 285 | rs28361009_A | 0.851 | 0.931 | 0.186 | 0.997 |
| 286 | rs9264879_C | 0.851 | 0.931 | 0.186 | 0.997 |
| 287 | rs9264881_A | 0.851 | 0.931 | 0.185 | 0.997 |
| 288 | rs9264882_T | 0.851 | 0.931 | 0.185 | 0.997 |
| 289 | rs9264883_G | 0.851 | 0.931 | 0.185 | 0.997 |
| 290 | rs9279098_A | 0.850 | 0.909 | 0.181 | 0.996 |
| 291 | rs9264886_G | 0.850 | 0.909 | 0.181 | 0.996 |
| 292 | rs9264892_G | 0.850 | 0.943 | 0.187 | 0.997 |
| 293 | rs9264893_T | 0.850 | 0.943 | 0.187 | 0.997 |
| 294 | rs9264924_A | 0.850 | 0.954 | 0.189 | 0.998 |
| 295 | rs9264925_A | 0.850 | 0.954 | 0.189 | 0.998 |
| 296 | rs9264926_T | 0.850 | 0.954 | 0.189 | 0.998 |
| 297 | rs2508006_C | 0.850 | 0.954 | 0.189 | 0.998 |
| 298 | rs77530144_C | 0.850 | 0.965 | 0.191 | 0.998 |
| 299 | rs376020605_T | 0.850 | 0.920 | 0.183 | 0.996 |
| 300 | rs9264856_G | 0.850 | 0.943 | 0.186 | 0.997 |
| 301 | rs9264857_A | 0.850 | 0.943 | 0.186 | 0.997 |
| 302 | rs9264887_G | 0.850 | 0.909 | 0.181 | 0.996 |
| 303 | rs9264889_C | 0.850 | 0.954 | 0.188 | 0.998 |
| 304 | rs9264891_T | 0.850 | 0.954 | 0.188 | 0.998 |
| 305 | rs9264852_G | 0.850 | 0.920 | 0.182 | 0.996 |
| 306 | rs9264853_G | 0.850 | 0.920 | 0.182 | 0.996 |
| 307 | rs9264854_A | 0.850 | 0.920 | 0.182 | 0.996 |
| 308 | rs532186099_C | 0.850 | 0.931 | 0.184 | 0.997 |
| 309 | rs9264890_A | 0.850 | 0.954 | 0.188 | 0.998 |
| 310 | rs9264931_C | 0.850 | 0.954 | 0.188 | 0.998 |

TABLE 3

Polymorphic markers in LD with HLA-B*57:01. PPV and
NPV refer to positive and negative predictive values,
respectively. In some cases, markers 1-19 of table
3 provide a panel of markers for HLA-B*57:01.

| Marker | SNP | specificity | sensitivity | ppv | npv |
|---|---|---|---|---|---|
| 1 | rs114170382_A | 0.997 | 1 | 0.967 | 1 |
| 2 | rs114607072_T | 0.997 | 0.993 | 0.967 | 0.999 |
| 3 | rs149663102_T | 0.997 | 0.986 | 0.961 | 0.999 |
| 4 | rs41558312_G | 0.997 | 0.993 | 0.961 | 0.999 |
| 5 | rs140810304_A | 0.997 | 0.993 | 0.961 | 0.999 |
| 6 | rs115841246_G | 0.997 | 0.993 | 0.961 | 0.999 |
| 7 | rs116081995_A | 0.997 | 0.993 | 0.961 | 0.999 |
| 8 | rs116339333_A | 0.997 | 0.993 | 0.961 | 0.999 |
| 9 | rs138130755_G | 0.997 | 0.993 | 0.961 | 0.999 |
| 10 | rs138117378_A | 0.997 | 0.993 | 0.961 | 0.999 |
| 11 | rs148792134_G | 0.997 | 0.993 | 0.961 | 0.999 |
| 12 | rs115986568_A | 0.997 | 0.993 | 0.955 | 0.999 |
| 13 | rs138099588_G | 0.997 | 0.993 | 0.955 | 0.999 |
| 14 | rs116419909_A | 0.997 | 0.993 | 0.955 | 0.999 |

TABLE 3-continued

Polymorphic markers in LD with HLA-B*57:01. PPV and
NPV refer to positive and negative predictive values,
respectively. In some cases, markers 1-19 of table
3 provide a panel of markers for HLA-B*57:01.

| Marker | SNP | specificity | sensitivity | ppv | npv |
|---|---|---|---|---|---|
| 15 | rs140991764_C | 0.997 | 0.986 | 0.955 | 0.999 |
| 16 | rs144027808_G | 0.996 | 0.993 | 0.949 | 0.999 |
| 17 | rs57989216_A | 0.985 | 1 | 0.816 | 1 |
| 18 | rs58102217_A | 0.985 | 1 | 0.816 | 1 |
| 19 | rs41543314_G | 0.985 | 1 | 0.811 | 1 |
| 20 | rs115846244_T | 0.994 | 0.986 | 0.914 | 0.999 |
| 21 | rs2395029_G | 0.993 | 0.986 | 0.908 | 0.999 |
| 22 | rs2905741_A | 0.992 | 0.927 | 0.891 | 0.995 |
| 23 | rs28732145_G | 0.991 | 0.887 | 0.875 | 0.992 |
| 24 | rs202036493_A | 0.990 | 0.993 | 0.872 | 0.999 |
| 25 | rs2923003_C | 0.990 | 0.993 | 0.867 | 0.999 |
| 26 | rs2516484_T | 0.989 | 0.907 | 0.845 | 0.994 |
| 27 | rs114118665_G | 0.986 | 0.966 | 0.824 | 0.997 |
| 28 | rs112168410_A | 0.985 | 1 | 0.816 | 1 |
| 29 | rs113223977_T | 0.985 | 0.993 | 0.815 | 0.999 |
| 30 | rs201415628_C | 0.985 | 0.986 | 0.814 | 0.999 |
| 31 | rs59440261_A | 0.983 | 0.993 | 0.789 | 0.999 |
| 32 | rs3021366_A | 0.980 | 0.927 | 0.752 | 0.995 |
| 33 | rs2905736_A | 0.980 | 0.927 | 0.752 | 0.995 |
| 34 | rs2905734_C | 0.980 | 0.927 | 0.752 | 0.995 |
| 35 | rs201725498_C | 0.980 | 0.854 | 0.737 | 0.990 |
| 36 | rs199923645_C | 0.980 | 0.854 | 0.737 | 0.990 |
| 37 | rs7757162_A | 0.980 | 0.907 | 0.748 | 0.993 |
| 38 | rs7757383_T | 0.980 | 0.913 | 0.75 | 0.994 |
| 39 | rs113688927_G | 0.979 | 1 | 0.758 | 1 |
| 40 | rs535476796. | 0.979 | 1 | 0.767 | 1 |
| | rs535476796. | | | | |
| | rs145010040_GTT | | | | |
| 41 | rs28732144_A | 0.978 | 0.900 | 0.727 | 0.993 |
| 42 | rs28895004_C | 0.977 | 0.880 | 0.718 | 0.992 |
| 43 | rs41293911_T | 0.977 | 0.907 | 0.724 | 0.993 |
| 44 | rs41293915_C | 0.977 | 0.907 | 0.724 | 0.993 |
| 45 | rs2516474_G | 0.977 | 0.907 | 0.724 | 0.993 |
| 46 | rs41293919_T | 0.977 | 0.907 | 0.724 | 0.993 |
| 47 | rs41293923_T | 0.977 | 0.907 | 0.724 | 0.993 |
| 48 | rs28732141_T | 0.977 | 0.907 | 0.724 | 0.993 |
| 49 | rs28732142_T | 0.977 | 0.907 | 0.724 | 0.993 |
| 50 | rs28732143_A | 0.977 | 0.907 | 0.724 | 0.993 |
| 51 | rs202125618_T | 0.977 | 0.907 | 0.724 | 0.993 |
| 52 | rs3093726_C | 0.977 | 0.907 | 0.724 | 0.993 |
| 53 | rs3093727_A | 0.977 | 0.907 | 0.724 | 0.993 |
| 54 | rs28895015_T | 0.977 | 0.887 | 0.720 | 0.992 |
| 55 | rs199682092_CATAT | 0.977 | 0.887 | 0.712 | 0.992 |
| 56 | rs17207190_A | 0.977 | 0.887 | 0.712 | 0.992 |
| 57 | rs13203101_A | 0.976 | 0.913 | 0.711 | 0.994 |
| 58 | rs28894981_T | 0.976 | 0.933 | 0.715 | 0.995 |
| 59 | rs28894982_T | 0.976 | 0.933 | 0.715 | 0.995 |
| 60 | rs141759545_A | 0.975 | 0.920 | 0.705 | 0.994 |
| 61 | rs13196399_G | 0.975 | 0.920 | 0.705 | 0.994 |
| 62 | rs28732096_A | 0.975 | 0.920 | 0.705 | 0.994 |
| 63 | rs28732101_T | 0.975 | 0.900 | 0.701 | 0.993 |
| 64 | rs28732081_A | 0.974 | 0.907 | 0.698 | 0.993 |
| 65 | rs28732099_A | 0.974 | 0.920 | 0.702 | 0.994 |
| 66 | rs537579418_T | 0.974 | 0.913 | 0.700 | 0.994 |
| 67 | rs28732100_T | 0.974 | 0.913 | 0.700 | 0.994 |
| 68 | rs531383859_T | 0.974 | 0.913 | 0.696 | 0.994 |
| 69 | rs112515516_G | 0.974 | 1 | 0.715 | 1 |
| 70 | rs563209172_G | 0.974 | 1 | 0.712 | 1 |
| 71 | rs1057151_C | 0.974 | 1 | 0.712 | 1 |
| 72 | rs111301312_G | 0.974 | 1 | 0.712 | 1 |
| 73 | rs151341415_G | 0.974 | 1 | 0.712 | 1 |
| 74 | rs41561016_T | 0.974 | 1 | 0.712 | 1 |
| 75 | rs1140487_T | 0.974 | 1 | 0.712 | 1 |
| 76 | rs41557415_G | 0.974 | 1 | 0.712 | 1 |
| 77 | rs41556417_C | 0.974 | 0.980 | 0.708 | 0.998 |
| 78 | rs147887806_T | 0.974 | 0.986 | 0.709 | 0.999 |
| 79 | rs28732097_G | 0.972 | 0.920 | 0.684 | 0.994 |
| 80 | rs111518019_A | 0.971 | 1 | 0.692 | 1 |
| 81 | rs28732093_T | 0.968 | 0.920 | 0.652 | 0.994 |
| 82 | rs144888775_A | 0.967 | 0.993 | 0.660 | 0.999 |
| 83 | rs199503730_T | 0.967 | 0.993 | 0.660 | 0.999 |
| 84 | rs113265260_TAC | 0.967 | 0.874 | 0.631 | 0.991 |
| 85 | rs112689184_A | 0.967 | 0.993 | 0.660 | 0.999 |

TABLE 3-continued

Polymorphic markers in LD with HLA-B*57:01. PPV and
NPV refer to positive and negative predictive values,
respectively. In some cases, markers 1-19 of table
3 provide a panel of markers for HLA-B*57:01.

| Marker | SNP | specificity | sensitivity | ppv | npv |
|---|---|---|---|---|---|
| 86 | rs79479695_T | 0.966 | 0.993 | 0.657 | 0.999 |
| 87 | rs75119533_A | 0.966 | 0.993 | 0.657 | 0.999 |
| 88 | rs79411911_T | 0.966 | 0.986 | 0.656 | 0.999 |
| 89 | rs201023435_C | 0.966 | 0.993 | 0.657 | 0.999 |
| 90 | rs74655380_G | 0.966 | 0.993 | 0.657 | 0.999 |
| 91 | rs77311173_T | 0.966 | 0.993 | 0.657 | 0.999 |
| 92 | rs13211972_A | 0.965 | 0.874 | 0.619 | 0.991 |
| 93 | rs13191258_T | 0.965 | 0.867 | 0.617 | 0.991 |
| 94 | rs28732088_A | 0.965 | 0.913 | 0.627 | 0.994 |
| 95 | rs17200095_G | 0.965 | 0.993 | 0.646 | 0.999 |
| 96 | rs13214865_T | 0.961 | 0.907 | 0.600 | 0.993 |
| 97 | rs73400361_G | 0.960 | 0.993 | 0.614 | 0.999 |
| 98 | rs41293856_T | 0.960 | 0.913 | 0.594 | 0.994 |
| 99 | rs13210132_G | 0.958 | 0.907 | 0.585 | 0.993 |
| 100 | rs28732080_C | 0.958 | 0.907 | 0.585 | 0.993 |
| 101 | rs577634159_C | 0.958 | 0.913 | 0.584 | 0.994 |
| 102 | rs41293899_T | 0.958 | 0.913 | 0.584 | 0.994 |
| 103 | rs41293883_T | 0.957 | 0.913 | 0.582 | 0.994 |
| 104 | rs41293887_A | 0.957 | 0.913 | 0.582 | 0.994 |
| 105 | rs41293895_C | 0.957 | 0.913 | 0.582 | 0.994 |
| 106 | rs41293860_A | 0.957 | 0.913 | 0.579 | 0.994 |
| 107 | rs3828917_T | 0.957 | 0.913 | 0.579 | 0.994 |
| 108 | rs41293879_A | 0.957 | 0.913 | 0.579 | 0.994 |
| 109 | rs4959077_A | 0.957 | 0.913 | 0.579 | 0.994 |
| 110 | rs41293891_A | 0.957 | 0.913 | 0.577 | 0.994 |
| 111 | rs4959078_A | 0.957 | 0.913 | 0.577 | 0.994 |
| 112 | rs41293907_T | 0.957 | 0.913 | 0.577 | 0.994 |
| 113 | rs111281598_C | 0.954 | 0.993 | 0.585 | 0.999 |
| 114 | rs3093668_C | 0.953 | 0.907 | 0.556 | 0.993 |
| 115 | rs3093661_A | 0.951 | 0.907 | 0.545 | 0.993 |
| 116 | rs12212594_C | 0.951 | 0.913 | 0.545 | 0.994 |
| 117 | rs2905725_T | 0.950 | 0.927 | 0.546 | 0.995 |
| 118 | rs146647111_AC | 0.949 | 1 | 0.557 | 1 |
| 119 | rs13210419_A | 0.947 | 0.940 | 0.533 | 0.995 |
| 120 | rs4947326_G | 0.935 | 0.907 | 0.475 | 0.993 |
| 121 | rs4947327_A | 0.935 | 0.907 | 0.475 | 0.993 |
| 122 | rs9267497_G | 0.935 | 0.907 | 0.475 | 0.993 |
| 123 | rs361525_A | 0.933 | 0.907 | 0.467 | 0.993 |
| 124 | rs112630608_C | 0.927 | 0.993 | 0.467 | 0.999 |
| 125 | rs112968142_G | 0.927 | 0.993 | 0.467 | 0.999 |
| 126 | rs9267454_T | 0.926 | 0.907 | 0.443 | 0.993 |
| 127 | rs9267466_T | 0.926 | 0.907 | 0.441 | 0.993 |
| 128 | rs2734576_C | 0.926 | 0.907 | 0.441 | 0.993 |
| 129 | rs9267492_T | 0.926 | 0.907 | 0.441 | 0.993 |
| 130 | rs9267456_A | 0.926 | 0.907 | 0.440 | 0.993 |
| 131 | rs9267457_T | 0.926 | 0.907 | 0.440 | 0.993 |
| 132 | rs4959079_T | 0.926 | 0.907 | 0.440 | 0.993 |
| 133 | rs9267461_G | 0.926 | 0.907 | 0.440 | 0.993 |
| 134 | rs9267462_C | 0.926 | 0.907 | 0.440 | 0.993 |
| 135 | rs9267463_A | 0.926 | 0.907 | 0.440 | 0.993 |
| 136 | rs9267464_T | 0.926 | 0.907 | 0.440 | 0.993 |
| 137 | rs9267465_A | 0.925 | 0.907 | 0.439 | 0.993 |
| 138 | rs9267487_C | 0.925 | 0.907 | 0.439 | 0.993 |
| 139 | rs28732092_T | 0.922 | 0.920 | 0.433 | 0.994 |
| 140 | rs113708600_C | 0.921 | 0.993 | 0.449 | 0.999 |
| 141 | rs1055821_T | 0.919 | 1 | 0.444 | 1 |
| 142 | rs76518703_G | 0.919 | 1 | 0.442 | 1 |
| 143 | rs566305135_T | 0.912 | 0.920 | 0.401 | 0.994 |
| 144 | rs2233956_C | 0.910 | 0.960 | 0.407 | 0.997 |
| 145 | rs28732089_G | 0.908 | 0.913 | 0.389 | 0.993 |
| 146 | rs368001137_T | 0.908 | 0.993 | 0.409 | 0.999 |
| 147 | rs28732087_T | 0.907 | 0.913 | 0.388 | 0.993 |
| 148 | rs4418214_C | 0.907 | 0.993 | 0.408 | 0.999 |
| 149 | rs28732082_A | 0.906 | 0.913 | 0.385 | 0.993 |
| 150 | rs3093553_G | 0.906 | 0.900 | 0.382 | 0.993 |
| 151 | rs12055599_C | 0.903 | 0.852 | 0.371 | 0.989 |
| 152 | rs141484466_C | 0.901 | 0.887 | 0.366 | 0.992 |
| 153 | rs28732138_A | 0.899 | 0.940 | 0.374 | 0.995 |
| 154 | rs3093664_G | 0.898 | 0.907 | 0.364 | 0.993 |
| 155 | rs12199223_A | 0.898 | 0.940 | 0.371 | 0.995 |
| 156 | rs12189871_T | 0.898 | 0.940 | 0.371 | 0.995 |
| 157 | rs12211087_A | 0.897 | 0.940 | 0.370 | 0.995 |
| 158 | rs28894993_T | 0.897 | 0.940 | 0.369 | 0.995 |

TABLE 3-continued

Polymorphic markers in LD with HLA-B*57:01. PPV and
NPV refer to positive and negative predictive values,
respectively. In some cases, markers 1-19 of table
3 provide a panel of markers for HLA-B*57:01.

| Marker | SNP | specificity | sensitivity | ppv | npv |
|---|---|---|---|---|---|
| 159 | rs564450374_C | 0.896 | 0.993 | 0.381 | 0.999 |
| 160 | rs4406273_A | 0.896 | 0.940 | 0.367 | 0.995 |
| 161 | rs3093662_G | 0.896 | 0.907 | 0.359 | 0.993 |
| 162 | rs28732084_C | 0.895 | 0.913 | 0.359 | 0.993 |
| 163 | rs28732086_A | 0.895 | 0.913 | 0.359 | 0.993 |
| 164 | rs28732083_C | 0.892 | 0.913 | 0.353 | 0.993 |
| 165 | rs559867198_G | 0.892 | 0.947 | 0.361 | 0.996 |
| 166 | rs375233420_T | 0.892 | 0.993 | 0.372 | 0.999 |
| 167 | rs9267502_A | 0.890 | 0.900 | 0.345 | 0.992 |
| 168 | rs114122095_G | 0.888 | 0.986 | 0.362 | 0.999 |
| 169 | rs3132514_C | 0.886 | 0.953 | 0.349 | 0.996 |
| 170 | rs28894977_C | 0.883 | 0.913 | 0.335 | 0.993 |
| 171 | rs59438896_T | 0.883 | 0.993 | 0.354 | 0.999 |
| 172 | rs76332236_C | 0.883 | 0.993 | 0.353 | 0.999 |
| 173 | rs112243036_A | 0.880 | 0.993 | 0.347 | 0.999 |
| 174 | rs1131201_C | 0.878 | 0.887 | 0.318 | 0.991 |
| 175 | rs1793893_C | 0.874 | 0.965 | 0.327 | 0.997 |
| 176 | rs527987255_G | 0.873 | 0.993 | 0.335 | 0.999 |
| 177 | rs34105339_C | 0.862 | 0.947 | 0.306 | 0.996 |
| 178 | rs1265178_A | 0.860 | 0.953 | 0.305 | 0.996 |
| 179 | rs1265177_G | 0.860 | 0.953 | 0.305 | 0.996 |
| 180 | rs561768797_A | 0.860 | 0.953 | 0.305 | 0.996 |
| 181 | rs78405443_C | 0.860 | 0.993 | 0.313 | 0.999 |
| 182 | rs1265181_C | 0.859 | 0.953 | 0.303 | 0.996 |
| 183 | rs1131446_T | 0.859 | 1 | 0.313 | 1 |
| 184 | rs73390248_T | 0.858 | 1 | 0.312 | 1 |
| 185 | rs28732090_G | 0.858 | 0.920 | 0.294 | 0.994 |
| 186 | rs35166487_AC | 0.856 | 0.920 | 0.292 | 0.994 |
| 187 | rs12195316_A | 0.856 | 0.920 | 0.292 | 0.994 |
| 188 | rs13198298_T | 0.856 | 0.920 | 0.291 | 0.994 |
| 189 | rs74594159_AG | 0.855 | 1 | 0.307 | 1 |
| 190 | rs28732157_T | 0.855 | 0.860 | 0.276 | 0.989 |
| 191 | rs9391731_A | 0.854 | 0.860 | 0.275 | 0.989 |
| 192 | rs9404941_C | 0.854 | 0.860 | 0.275 | 0.989 |
| 193 | rs2280801_T | 0.854 | 0.860 | 0.274 | 0.989 |
| 194 | rs2295663_G | 0.854 | 0.860 | 0.274 | 0.989 |
| 195 | rs1639110_A | 0.853 | 0.966 | 0.297 | 0.997 |
| 196 | rs1793895_T | 0.853 | 0.966 | 0.297 | 0.997 |
| 197 | rs3087617_T | 0.853 | 0.913 | 0.285 | 0.993 |
| 198 | rs28732154_T | 0.853 | 0.854 | 0.272 | 0.989 |
| 199 | rs28732150_A | 0.852 | 0.860 | 0.273 | 0.989 |
| 200 | rs527864796_A | 0.852 | 0.966 | 0.295 | 0.997 |
| 201 | rs9380266_C | 0.851 | 0.860 | 0.271 | 0.989 |
| 202 | rs9378164_A | 0.851 | 0.860 | 0.271 | 0.989 |
| 203 | rs28732158_G | 0.851 | 0.860 | 0.276 | 0.989 |

TABLE 4

Polymorphic markers in LD with HLA-B*58:01. PPV and
NPV refer to positive and negative predictive values,
respectively. In some cases, markers 1-4 of table
4 provide a panel of markers for HLA-B*58:01.

| Marker | SNP | specificity | sensitivity | ppv | npv |
|---|---|---|---|---|---|
| 1 | rs78090769_T | 0.979 | 0.994 | 0.772 | 0.999 |
| 2 | rs79815527_A | 0.977 | 0.970 | 0.757 | 0.997 |
| 3 | rs75412754_C | 0.977 | 0.958 | 0.754 | 0.996 |
| 4 | rs143527370_TTA | 0.975 | 0.934 | 0.732 | 0.995 |
| 5 | rs7769586_T | 0.855 | 0.970 | 0.324 | 0.997 |
| 6 | rs9264041_G | 0.855 | 0.970 | 0.324 | 0.997 |
| 7 | rs7739334_C | 0.853 | 0.970 | 0.321 | 0.997 |
| 8 | rs9264132_C | 0.854 | 0.970 | 0.322 | 0.997 |
| 9 | rs542772601_TA | 0.854 | 0.970 | 0.322 | 0.997 |
| 10 | rs4084090_G | 0.853 | 0.970 | 0.321 | 0.997 |
| 11 | rs4416711_T | 0.851 | 0.970 | 0.318 | 0.997 |
| 12 | rs141484466_C | 0.907 | 0.898 | 0.409 | 0.992 |
| 13 | rs1131201_C | 0.883 | 0.886 | 0.351 | 0.990 |
| 14 | rs1131214_C | 0.899 | 0.868 | 0.380 | 0.989 |
| 15 | rs1140404_G | 0.899 | 0.868 | 0.380 | 0.989 |

TABLE 4-continued

Polymorphic markers in LD with HLA-B*58:01. PPV and
NPV refer to positive and negative predictive values,
respectively. In some cases, markers 1-4 of table
4 provide a panel of markers for HLA-B*58:01.

| Marker | SNP | specificity | sensitivity | ppv | npv |
|---|---|---|---|---|---|
| 16 | rs41541616_C | 0.897 | 0.856 | 0.374 | 0.988 |
| 17 | rs41543121_T | 0.899 | 0.856 | 0.378 | 0.988 |

TABLE 5

Polymorphic markers in LD with HLA-B*58:02, an allele related
to HLA- B*58:01. PPV and NPV refer to positive and negative
predictive values, respectively. In some cases, the marker(s)
of Table 5 (e.g., markers 1-2) for allele HLA-B*58:02 can
be assessed and distinguished from the panel of assessed
markers of Table 4, to provide further specificity for assessing
ADR risks associated with allele HLA-B*58:01.

| Marker | SNP | specificity | sensitivity | ppv | npv |
|---|---|---|---|---|---|
| 1 | rs6936478_A | 0.997 | 1 | 0.878 | 1 |
| 2 | rs111664408_G | 0.997 | 0.972 | 0.833 | 0.999 |
| 3 | rs12199223_A | 0.859 | 1 | 0.094 | 1 |
| 4 | rs12189871_T | 0.859 | 1 | 0.094 | 1 |
| 5 | rs4406273_A | 0.858 | 1 | 0.093 | 1 |
| 6 | rs12211087_A | 0.859 | 1 | 0.093 | 1 |
| 7 | rs28894993_T | 0.858 | 1 | 0.093 | 1 |
| 8 | rs28732138_A | 0.861 | 1 | 0.094 | 1 |
| 9 | rs78090769_T | 0.927 | 1 | 0.167 | 1 |
| 10 | rs79815527_A | 0.927 | 0.972 | 0.163 | 0.999 |
| 11 | rs75412754_C | 0.928 | 0.972 | 0.165 | 0.999 |
| 12 | rs143527370_TTA | 0.927 | 0.972 | 0.164 | 0.999 |
| 13 | rs534234550_G | 0.881 | 0.972 | 0.107 | 0.999 |
| 14 | rs9267184_T | 0.881 | 0.972 | 0.107 | 0.999 |
| 15 | rs67942473_T | 0.881 | 0.972 | 0.107 | 0.999 |
| 16 | rs9267202_A | 0.881 | 0.972 | 0.107 | 0.999 |
| 17 | rs9267212_T | 0.881 | 0.972 | 0.107 | 0.999 |
| 18 | rs9267214_T | 0.881 | 0.972 | 0.107 | 0.999 |
| 19 | rs537357246_A | 0.882 | 0.972 | 0.108 | 0.999 |
| 20 | rs9267217_C | 0.881 | 0.972 | 0.107 | 0.999 |
| 21 | rs9267218_A | 0.882 | 0.972 | 0.107 | 0.999 |
| 22 | rs541349280_A | 0.884 | 0.972 | 0.109 | 0.999 |
| 23 | rs9267271_A | 0.861 | 0.972 | 0.092 | 0.999 |
| 24 | rs9267280_A | 0.881 | 0.972 | 0.107 | 0.999 |
| 25 | rs9267283_A | 0.875 | 0.972 | 0.102 | 0.999 |
| 26 | rs9267289_A | 0.881 | 0.972 | 0.107 | 0.999 |
| 27 | rs9267296_A | 0.881 | 0.972 | 0.106 | 0.999 |
| 28 | rs9267301_C | 0.882 | 0.972 | 0.107 | 0.999 |
| 29 | rs2523460_A | 0.881 | 0.972 | 0.107 | 0.999 |
| 30 | rs9267315_T | 0.881 | 0.972 | 0.107 | 0.999 |
| 31 | rs143499322_C | 0.997 | 0.944 | 0.871 | 0.999 |
| 32 | rs79503523_G | 0.951 | 0.944 | 0.220 | 0.999 |
| 33 | rs148725606_A | 0.908 | 0.944 | 0.130 | 0.999 |
| 34 | rs9267133_A | 0.908 | 0.944 | 0.130 | 0.999 |
| 35 | rs2395031_A | 0.906 | 0.944 | 0.128 | 0.999 |
| 36 | rs2894220_T | 0.907 | 0.944 | 0.129 | 0.999 |
| 37 | rs9267135_C | 0.907 | 0.944 | 0.129 | 0.999 |
| 38 | rs9267136_A | 0.907 | 0.944 | 0.129 | 0.999 |
| 39 | rs9267137_C | 0.907 | 0.944 | 0.129 | 0.999 |
| 40 | rs7758090_T | 0.891 | 0.944 | 0.112 | 0.999 |
| 41 | rs7758267_A | 0.891 | 0.944 | 0.112 | 0.999 |
| 42 | rs9267141_T | 0.891 | 0.944 | 0.112 | 0.999 |
| 43 | rs9267142_G | 0.891 | 0.944 | 0.112 | 0.999 |
| 44 | rs9267143_T | 0.891 | 0.944 | 0.112 | 0.999 |
| 45 | rs9267145_G | 0.891 | 0.944 | 0.112 | 0.999 |
| 46 | rs9267146_G | 0.891 | 0.944 | 0.112 | 0.999 |
| 47 | rs9267147_C | 0.891 | 0.944 | 0.112 | 0.999 |
| 48 | rs576159127_CT | 0.879 | 0.944 | 0.102 | 0.999 |
| 49 | rs9267155_G | 0.879 | 0.944 | 0.102 | 0.999 |
| 50 | rs9267156_T | 0.879 | 0.944 | 0.102 | 0.999 |
| 51 | rs9267157_T | 0.880 | 0.944 | 0.103 | 0.999 |
| 52 | rs9267168_A | 0.891 | 0.944 | 0.112 | 0.999 |
| 53 | rs9267169_T | 0.891 | 0.944 | 0.112 | 0.999 |
| 54 | rs3828893_A | 0.891 | 0.944 | 0.112 | 0.999 |
| 55 | rs3749945_T | 0.891 | 0.944 | 0.112 | 0.999 |

TABLE 5-continued

Polymorphic markers in LD with HLA-B*58:02, an allele related
to HLA- B*58:01. PPV and NPV refer to positive and negative
predictive values, respectively. In some cases, the marker(s)
of Table 5 (e.g., markers 1-2) for allele HLA-B*58:02 can
be assessed and distinguished from the panel of assessed
markers of Table 4, to provide further specificity for assessing
ADR risks associated with allele HLA-B*58:01.

| Marker | SNP | specificity | sensitivity | ppv | npv |
|---|---|---|---|---|---|
| 56 | rs72459742_A | 0.891 | 0.944 | 0.112 | 0.999 |
| 57 | rs9267175_T | 0.891 | 0.944 | 0.112 | 0.999 |
| 58 | rs9267176_T | 0.891 | 0.944 | 0.112 | 0.999 |
| 59 | rs9267211_T | 0.882 | 0.944 | 0.104 | 0.999 |
| 60 | rs200587233_G | 0.885 | 0.944 | 0.107 | 0.999 |
| 61 | rs9267243_T | 0.882 | 0.944 | 0.104 | 0.999 |
| 62 | rs17197066_A | 0.997 | 0.916 | 0.846 | 0.998 |
| 63 | rs147200847_A | 0.994 | 0.916 | 0.717 | 0.998 |
| 64 | rs112928571_G | 0.997 | 0.916 | 0.846 | 0.998 |
| 65 | rs182979559_T | 0.997 | 0.916 | 0.846 | 0.998 |
| 66 | rs572558969_G | 0.997 | 0.916 | 0.846 | 0.998 |
| 67 | rs7752002_T | 0.997 | 0.916 | 0.868 | 0.998 |
| 68 | rs6934570_G | 0.946 | 0.916 | 0.201 | 0.998 |
| 69 | rs187331993_T | 0.995 | 0.916 | 0.767 | 0.998 |
| 70 | rs1793894_A | 0.915 | 0.916 | 0.136 | 0.998 |
| 71 | rs527277270. rs531277843_G | 0.921 | 0.916 | 0.146 | 0.998 |
| 72 | rs16899682_C | 0.952 | 0.888 | 0.214 | 0.998 |
| 73 | rs146870705_T | 0.997 | 0.888 | 0.842 | 0.998 |
| 74 | rs62395345_G | 0.971 | 0.888 | 0.310 | 0.998 |
| 75 | rs13197153_C | 0.946 | 0.888 | 0.196 | 0.998 |
| 76 | rs149345291_A | 0.891 | 0.861 | 0.103 | 0.997 |
| 77 | rs549439680_T | 0.985 | 0.861 | 0.469 | 0.997 |
| 78 | rs140577688_G | 0.997 | 0.861 | 0.861 | 0.997 |
| 79 | rs112625334_C | 0.974 | 0.861 | 0.329 | 0.997 |
| 80 | rs112193896_T | 0.974 | 0.861 | 0.326 | 0.997 |
| 81 | rs113807067_A | 0.988 | 0.861 | 0.516 | 0.997 |
| 82 | rs114910910_C | 0.988 | 0.861 | 0.516 | 0.997 |
| 83 | rs111541554_G | 0.990 | 0.861 | 0.563 | 0.997 |
| 84 | rs114500081_A | 0.988 | 0.861 | 0.525 | 0.997 |
| 85 | rs62395767_G | 0.978 | 0.861 | 0.369 | 0.997 |
| 86 | rs3093667_T | 0.997 | 0.861 | 0.815 | 0.997 |
| 87 | rs3093669_A | 0.987 | 0.861 | 0.492 | 0.997 |
| 88 | rs115166054_T | 0.989 | 0.861 | 0.534 | 0.997 |
| 89 | rs148897498_C | 0.988 | 0.861 | 0.525 | 0.997 |
| 90 | rs140894428_C | 0.988 | 0.861 | 0.525 | 0.997 |
| 91 | rs145103532_C | 0.997 | 0.861 | 0.861 | 0.997 |

Example 2: Polymorphic Markers for Pharmacogenetic HLA Risk Alleles

Methodology

Specific HLA alleles strongly associated with drug toxicities/response with a PharmGKB strength of evidence score of ≥2 were selected from the PharmGKB database (see Whirl-Carrillo, M., et al., Pharmacogenomics knowledge for personalized medicine. Clin Pharmacol Ther, 2012. 92(4): p. 414-7) for subsequent discovery of proxy-single nucleotide polymorphism (proxy-SNP) markers. We identified 2504 samples from the 1000 Genomes (1KG) Project dataset that had both whole genome sequencing and HLA typing data available (discovery cohort) (see Abi-Rached, L., et al., Immune diversity sheds light on missing variation in worldwide genetic diversity panels. PLoS One, 2018. 13(10): p. e0206512; and Genomes Project, C., et al., A global reference for human genetic variation. Nature, 2015. 526(7571): p. 68-74).

These multi-ethnic samples represented the five super populations, as defined by the 1KG Project: African Americans (n=661), Europeans (n=503), Hispanics (n=347), East (n=504) and South Asians (n=489). We evaluated the performance of all variants within the MHC region (n=608,256) across the entire discovery cohort to tag the selected pharmacogenetic HLA alleles by assessing their sensitivity, specificity, positive predictive value, and negative predictive value (Erlichster, M., et al., Cross-ethnicity tagging SNPs for HLA alleles associated with adverse drug reaction. Pharmacogenomics J, 2018). The identified proxy-SNPs were ranked based on these performance metrics, which informs the selection of multi-ethnic proxy-SNPs as markers of pharmacogenetic HLA risk alleles. In addition, the initial performance metric estimations of the high ranking proxy-SNPs were refined by experimentally genotyping and/or HLA typing selected samples with potential false positive and/or false negative results based on the low-coverage sequencing data of the 1KG Project. Of note, this analysis also identified some proxy-SNPs that are markers for highly related HLA risk alleles with only recent evolutionary divergence (e.g., B*58:01 and B*58:02). To confirm the performance metrics of the identified top ranking proxy-SNPs, an independent replication cohort of 79 multi-ethnic Coriell samples was analyzed [African Americans (n=20), Europeans (n=27), Hispanics (n=8), East Asians (n=23) and Middle Eastern (n=1)], which included 60 samples confirmed to carry at least one of the pharmacogenetic HLA risk alleles (Abi-Rached, L., et al., PLoS One, 2018. 13(10): p. e0206512; Bettinotti, M. P., et al., Characterization of 108 Genomic DNA Reference Materials for 11 Human Leukocyte Antigen Loci: A GeT-RM Collaborative Project. J Mol Diagn, 2018. 20(5): p. 703-715; and Bykova et al., In Silico Analysis of the Minor Histocompatibility Antigen Landscape Based on the 1000 Genomes Project. Front Immunol, 2018. 9: p. 1819).

Results

Further analysis was performed to identify smaller panels of the best proxy-SNPs for the HLA alleles. As described above, 2504 samples across super populations from 1000 Genome project dataset with whole genome sequencing and HLA typing data (discovery cohort, FIG. 1). We estimated the carriage sensibility and specificity to assess the HLA allele tagging performance of each variant within MHC region (n=608,256). We typed false positive and false negative samples to confirm the predicted estimations for the best proxy-SNPs. We genotyped those proxy-SNPs on 79 multiethnic samples, 60 of which carry at least one of the four HLA alleles (Replication cohort, FIG. 1) to confirm sensibility and sensitivity of selected SNPs in an independent cohort.

The results of this analysis are presented in Tables 6 and 7. Our findings identified a novel multi-ethic proxy-SNP panel that could enable cost-effective and rapid genotype-based screening to predict the four major FDA/EMA recommended pharmacogenomic HLA risk alleles.

TABLE 6

Sensitivity (SN) and specificity (SP) of the selected proxy-SNPs for HLA-A*31:01, HLA-B*15:02, HLA-B*58:01 and HLA-B*57:01.

| Probe name | Discovery (n = 2504) | | | | Replication (n = 79) | | | |
|---|---|---|---|---|---|---|---|---|
| | SN | SP | PPV | NPV | SN | SP | PPV | NPV |
| HLA-A*31:01 | | | | | | | | |
| rs114776910__G | 0.976 | 0.999 | 0.984 | 0.999 | 1.000 | 1.000 | 1.000 | 1.000 |
| rs138415245__G | 0.952 | 0.999 | 0.984 | 0.997 | 1.000 | 1.000 | 1.000 | 1.000 |
| rs12665140__A | 0.968 | 0.999 | 0.984 | 0.998 | 1.000 | 1.000 | 1.000 | 1.000 |
| rs147023494__T | 1.000 | 0.997 | 0.955 | 1.000 | 1.000 | 1.000 | 1.000 | 1.000 |
| rs148590958__C | 0.944 | 0.998 | 0.967 | 0.997 | 1.000 | 1.000 | 1.000 | 1.000 |
| rs114716190__G | 0.952 | 0.998 | 0.968 | 0.997 | 1.000 | 1.000 | 1.000 | 1.000 |
| HLA-B*15:02 | | | | | | | | |
| rs144012689__A | 1.000 | 1.000 | 1.000 | 1.000 | | | | |
| rs151107659__A | 1.000 | 1.000 | 1.000 | 1.000 | 1.000 | 1.000 | 1.000 | 1.000 |
| rs188729361__A | 0.989 | 1.000 | 1.000 | 1.000 | 1.000 | 1.000 | 1.000 | 1.000 |
| rs181377228__A | 0.989 | 0.990 | 1.000 | 1.000 | 1.000 | 1.000 | 1.000 | 1.000 |
| HLA-B*58:01 | | | | | | | | |
| rs78090769_T | 0.994 | 0.996 | 0.949 | 1.000 | 1.000 | 1.000 | 1.000 | 1.000 |
| rs79815527_A | 0.970 | 0.994 | 0.926 | 0.998 | 0.950 | 1.000 | 1.000 | 0.984 |
| rs75412754__C | 0.970 | 0.994 | 0.926 | 0.998 | 0.950 | 1.000 | 1.000 | 0.984 |
| rs6936478__A | 1.000 | 0.996 | 0.878 | 1.000 | | | | |
| HLA-B*57:01 | | | | | | | | |
| rs115986568__A | 1.000 | 0.998 | 0.968 | 1.000 | 1.000 | 1.000 | 1.000 | 1.000 |
| rs149663102__T | 1.000 | 0.998 | 0.968 | 1.000 | 1.000 | 1.000 | 1.000 | 1.000 |
| rs114170382__A | 1.000 | 0.998 | 0.968 | 1.000 | 1.000 | 1.000 | 1.000 | 1.000 |
| rs114607072__T | 0.993 | 0.998 | 0.968 | 1.000 | 1.000 | 1.000 | 1.000 | 1.000 |
| rs138099588__G | 0.993 | 0.997 | 0.955 | 1.000 | 1.000 | 1.000 | 1.000 | 1.000 |
| rs41558312__G | 0.993 | 0.998 | 0.968 | 1.000 | 1.000 | 1.000 | 1.000 | 1.000 |
| rs58102217__A | 1.000 | 0.986 | 0.816 | 1.000 | 1.000 | 0.982 | 0.930 | 1.000 |
| rs41543314__G | 1.000 | 0.985 | 0.812 | 1.000 | 1.000 | 1.000 | 1.000 | 1.000 |

PPV positive predictive value.
NPV negative predictive value.

TABLE 7

Sensitivity (SN) and specificity (SP) by ethnicities (reported the number of carriers) of selected proxy-SNPs for HLA-A*31:01, HLA-B*15:02, HLA-B*58:01 and HLA-B*57:01.

HLA-A*31:01

| probe name | African Americans (n = 10) | | | | Hispanics (n = 32) | | | | Europeans (n = 24) | |
|---|---|---|---|---|---|---|---|---|---|---|
|  | SS | SP | PPV | NPV | SS | SP | PPV | NPV | SS | SP |
| rs114776910_G | 0.70 | 1.00 | 1.00 | 1.00 | 1.00 | 1.00 | 1.00 | 1.00 | 1.00 | 1.00 |
| rs138415245_G | 0.60 | 1.00 | 1.00 | 0.99 | 1.00 | 1.00 | 1.00 | 1.00 | 1.00 | 1.00 |
| rs12665140_A | 0.60 | 1.00 | 1.00 | 0.99 | 1.00 | 1.00 | 1.00 | 1.00 | 1.00 | 1.00 |
| rs147023494_T | 1.00 | 0.99 | 0.71 | 1.00 | 1.00 | 1.00 | 1.00 | 1.00 | 1.00 | 1.00 |
| rs148590958_C | 0.60 | 1.00 | 1.00 | 0.99 | 1.00 | 1.00 | 0.97 | 1.00 | 0.92 | 1.00 |
| rs114716190_G | 0.70 | 1.00 | 1.00 | 1.00 | 1.00 | 1.00 | 0.97 | 1.00 | 0.92 | 1.00 |

| probe name | Europeans (n = 24) | | East Asians (n = 36) | | | | South Asians (n = 24) | | | |
|---|---|---|---|---|---|---|---|---|---|---|
|  | PPV | NPV | SS | SP | PPV | NPV | SS | SP | PPV | NPV |
| rs114776910_G | 1.00 | 1.00 | 1.00 | 1.00 | 1.00 | 1.00 | 1.00 | 1.00 | 0.92 | 1.00 |
| rs138415245_G | 1.00 | 1.00 | 0.97 | 1.00 | 1.00 | 1.00 | 1.00 | 1.00 | 0.92 | 1.00 |
| rs12665140_A | 1.00 | 1.00 | 1.00 | 1.00 | 1.00 | 1.00 | 1.00 | 1.00 | 0.92 | 1.00 |
| rs147023494_T | 1.00 | 1.00 | 1.00 | 1.00 | 1.00 | 1.00 | 1.00 | 1.00 | 0.92 | 1.00 |
| rs148590958_C | 1.00 | 1.00 | 0.97 | 1.00 | 0.97 | 1.00 | 1.00 | 1.00 | 0.92 | 1.00 |
| rs114716190_G | 1.00 | 1.00 | 0.97 | 1.00 | 0.97 | 1.00 | 1.00 | 1.00 | 0.92 | 1.00 |

HLA-B*15:02

| probe name | African Americans | | | | Hispanics | | | | Europeans | |
|---|---|---|---|---|---|---|---|---|---|---|
|  | SS | SP | PPV | NPV | SS | SP | PPV | NPV | SS | SP |
| rs144012689_A |  |  |  |  |  |  |  |  |  |  |
| rs151107659_A |  |  |  |  |  |  |  |  |  |  |
| rs188729361_A |  |  |  |  |  |  |  |  |  |  |
| rs181377228_A |  |  |  |  |  |  |  |  |  |  |

| probe name | Europeans | | East Asians (n = 47) | | | | South Asians (n = 41) | | | |
|---|---|---|---|---|---|---|---|---|---|---|
|  | PPV | NPV | SS | SP | PPV | NPV | SS | SP | PPV | NPV |
| rs144012689_A |  |  | 1.00 | 1.00 | 1.00 | 1.00 | 1.00 | 1.00 | 1.00 | 1.00 |
| rs151107659_A |  |  | 1.00 | 1.00 | 1.00 | 1.00 | 1.00 | 1.00 | 1.00 | 1.00 |
| rs188729361_A |  |  | 0.98 | 1.00 | 1.00 | 1.00 | 1.00 | 1.00 | 1.00 | 1.00 |
| rs181377228_A |  |  | 0.98 | 1.00 | 1.00 | 1.00 | 1.00 | 1.00 | 1.00 | 1.00 |

HLA-B*58:01

| probe name | African Americans (n = 71) | | | | Hispanics (n = 5) | | | | Europeans (n = 8) | |
|---|---|---|---|---|---|---|---|---|---|---|
|  | SS | SP | PPV | NPV | SS | SP | PPV | NPV | SS | SP |
| rs78090769_T | 0.99 | 0.99 | 0.90 | 1.00 | 1.00 | 1.00 | 1.00 | 1.00 | 1.00 | 1.00 |
| rs79815527_A | 0.93 | 0.98 | 0.88 | 0.99 | 1.00 | 0.99 | 0.63 | 1.00 | 1.00 | 1.00 |
| rs75412754_C | 0.93 | 0.98 | 0.88 | 0.99 | 1.00 | 0.99 | 0.63 | 1.00 | 1.00 | 1.00 |
| rs6936478_A | 1.00 | 0.99 | 0.87 | 1.00 | 1.00 | 1.00 | 1.00 | 1.00 |  |  |

| probe name | Europeans (n = 8) | | East Asians (n = 55) | | | | South Asians (n = 28) | | | |
|---|---|---|---|---|---|---|---|---|---|---|
|  | PPV | NPV | SS | SP | PPV | NPV | SS | SP | PPV | NPV |
| rs78090769_T | 1.00 | 1.00 | 1.00 | 1.00 | 1.00 | 1.00 | 1.00 | 1.00 | 0.97 | 1.00 |
| rs79815527_A | 1.00 | 1.00 | 1.00 | 1.00 | 1.00 | 1.00 | 1.00 | 1.00 | 0.97 | 1.00 |
| rs75412754_C | 1.00 | 1.00 | 1.00 | 1.00 | 1.00 | 1.00 | 1.00 | 1.00 | 0.97 | 1.00 |
| rs6936478_A |  |  |  |  |  |  |  |  |  |  |

TABLE 7-continued

Sensitivity (SN) and specificity (SP) by ethnicities (reported
the number of carriers) of selected proxy-SNPs for HLA-
A*31:01, HLA-B*15:02, HLA-B*58:01 and HLA-B*57:01.

HLA-B*57:01

| | African Americans (n = 1) | | | | Hispanics (n = 12) | | | | Europeans (n = 42) | |
|---|---|---|---|---|---|---|---|---|---|---|
| probe name | SS | SP | PPV | NPV | SS | SP | PPV | NPV | SS | SP |
| rs115986568__A | 1.00 | 1.00 | 1.00 | 1.00 | 1.00 | 1.00 | 0.92 | 1.00 | 1.00 | 1.00 |
| rs149663102__T | 1.00 | 1.00 | 1.00 | 1.00 | 1.00 | 1.00 | 0.92 | 1.00 | 1.00 | 1.00 |
| rs114170382__A | 1.00 | 1.00 | 1.00 | 1.00 | 1.00 | 1.00 | 0.92 | 1.00 | 1.00 | 1.00 |
| rs114607072__T | 1.00 | 1.00 | 1.00 | 1.00 | 1.00 | 1.00 | 0.92 | 1.00 | 0.98 | 1.00 |
| rs138099588__G | 1.00 | 1.00 | 0.50 | 1.00 | 1.00 | 1.00 | 0.92 | 1.00 | 0.98 | 1.00 |
| rs41558312__G | 1.00 | 1.00 | 1.00 | 1.00 | 1.00 | 1.00 | 1.00 | 1.00 | 0.98 | 1.00 |
| rs58102217__A | 1.00 | 0.96 | 0.04 | 1.00 | 1.00 | 0.99 | 0.86 | 1.00 | 1.00 | 0.99 |
| rs41543314__G | 1.00 | 0.96 | 0.04 | 1.00 | 1.00 | 0.98 | 0.67 | 1.00 | 1.00 | 1.00 |

| | Europeans (n = 42) | | East Asians (n = 11) | | | | South Asians (n = 85) | | | |
|---|---|---|---|---|---|---|---|---|---|---|
| probe name | PPV | NPV | SS | SP | PPV | NPV | SS | SP | PPV | NPV |
| rs115986568__A | 0.98 | 1.00 | 1.00 | 1.00 | 1.00 | 1.00 | 1.00 | 0.99 | 0.97 | 1.00 |
| rs149663102__T | 0.98 | 1.00 | 1.00 | 1.00 | 1.00 | 1.00 | 1.00 | 0.99 | 0.97 | 1.00 |
| rs114170382__A | 0.98 | 1.00 | 1.00 | 1.00 | 1.00 | 1.00 | 1.00 | 0.99 | 0.97 | 1.00 |
| rs114607072__T | 0.98 | 1.00 | 1.00 | 1.00 | 1.00 | 1.00 | 1.00 | 0.99 | 0.97 | 1.00 |
| rs138099588__G | 0.95 | 1.00 | 1.00 | 1.00 | 1.00 | 1.00 | 1.00 | 0.99 | 0.97 | 1.00 |
| rs41558312__G | 0.95 | 1.00 | 1.00 | 1.00 | 1.00 | 1.00 | 1.00 | 0.99 | 0.97 | 1.00 |
| rs58102217__A | 0.93 | 1.00 | 1.00 | 1.00 | 1.00 | 1.00 | 1.00 | 0.99 | 0.97 | 1.00 |
| rs41543314__G | 0.95 | 1.00 | 1.00 | 1.00 | 1.00 | 1.00 | 1.00 | 0.99 | 0.97 | 1.00 |

PPV positive predictive value.
NPV negative predictive value.

What is claimed is:

1. A method comprising:
(a) assaying for one or more genetic markers each independently selected from rs114776910_G, rs138415245_G, rs12665140_A, rs148590958_C, and rs114716190_G, in a sample from a subject,
wherein the one or more genetic markers are in linkage disequilibrium with an HLA allele associated with the ADR and selected from HLA-A*31:01, HLA-B*15:02, HLA-B*57:01, and HLA-B*58:01;
(b) assessing a risk of adverse drug reaction (ADR) in the subject in response to a drug associated with the ADR,
wherein an elevated risk is assessed when the one or more genetic markers are present in the sample and an average risk is assessed when the one or more genetic markers are absent from the sample,
wherein the assessing comprises detecting a presence or absence of the HLA allele in the subject based on the one or more genetic markers,
wherein the detecting has a positive predictive value of at least 0.92 and a negative predictive value of at least 0.99 across a set of multi-ethnic populations,
wherein the set of multi-ethnic populations comprises an African American population, a European population, a Hispanic population, an East Asian population, and a South Asian population; and
(c) administering the drug to the subject when an average risk of the ADR is assessed in the subject, or declining to administer the drug to the subject when an elevated risk of the ADR is assessed in the subject;
wherein the drug is capable of treating a disease or condition of the subject; and wherein the disease or condition of the subject comprises human immunodeficiency virus (HIV)/acquired immunodeficiency syndrome (AIDS), epilepsy, gout, neuropathic pain, a mood disorder, anxiety, kidney stones, or chemotherapy side effects.

2. The method of claim 1, wherein the drug is selected from abacavir, carbamazepine, phenytoin, and allopurinol.

3. The method of claim 1, wherein the ADR is selected from acute hepatitis, hypersensitivity syndrome, Stevens-Johnson syndrome (SJS), toxic epidermal necrolysis (TEN), and mild cutaneous ADR.

4. The method of claim 1, wherein the sample from the subject is selected from saliva, urine, whole blood, plasma, serum, peripheral blood, and hair.

5. The method of claim 1, wherein the assaying comprises isolating or amplifying genomic deoxyribonucleic acid (DNA) from the subject.

6. The method of claim 1, wherein the assaying comprises sequencing, selective hybridization, or selective amplification.

7. The method of claim 1, wherein:
an average risk of the ADR in the subject is assessed when all of the one or more genetic markers for the HLA allele that are assayed are absent; and
an elevated risk of the ADR in the subject is assessed when all of the one or more genetic markers for the HLA allele that are assayed are present.

8. The method of claim 1, wherein the detecting has an average of 99% sensitivity and 99% specificity across the set of multi-ethnic populations.

* * * * *